US006955650B2

(12) United States Patent
Mault et al.

(10) Patent No.: US 6,955,650 B2
(45) Date of Patent: *Oct. 18, 2005

(54) METABOLIC CALORIMETER EMPLOYING RESPIRATORY GAS ANALYSIS

(75) Inventors: James R. Mault, Evergreen, CO (US); Edwin M. Pearce, Jr., San Francisco, CA (US); Theodore W. Barber, Belmont, CA (US); Craig M. Lawrence, Menlo Park, CA (US); Timothy J. Prachar, Palo Alto, CA (US); Jeffrey C. Weintraub, San Jose, CA (US); Kevin S. Nason, Mountain View, CA (US)

(73) Assignee: HealtheTech, Inc., Golden, CO (US)

( * ) Notice: Subject to any disclaimer, the term of this patent is extended or adjusted under 35 U.S.C. 154(b) by 42 days.

This patent is subject to a terminal disclaimer.

(21) Appl. No.: 10/161,244

(22) Filed: May 31, 2002

(65) Prior Publication Data

US 2003/0065273 A1 Apr. 3, 2003

Related U.S. Application Data

(63) Continuation of application No. 09/630,398, filed on Aug. 2, 2000, now Pat. No. 6,468,222
(60) Provisional application No. 60/146,898, filed on Aug. 2, 1999, provisional application No. 60/155,035, filed on Sep. 20, 1999, provisional application No. 60/219,241, filed on Jul. 18, 2000, and provisional application No. 60/218,863, filed on Jul. 18, 2000.

(51) Int. Cl.[7] .............................................. A61B 5/08
(52) U.S. Cl. ...................................... 600/531; 600/529
(58) Field of Search ................................ 600/529–543; 73/23.3; 128/204.18, 200.24, 205.12, 205.27, 206.12, 206.15–206.17, 206.22, 206.24, 909; D24/110.1

(56) References Cited

U.S. PATENT DOCUMENTS 2,249,867 A    7/1941  Snelling .................. 73/335.08

(Continued)

FOREIGN PATENT DOCUMENTS

DE    198 10 476    9/1998

(Continued)

OTHER PUBLICATIONS

Medical Progress Through Technology, vol. 9, No. 1, 1982, Berlin (D), pp. 27–32, R. Salninen et al., "Computerized Breath–By–Breath Analysis of Respiratory Variables During Exercise".

(Continued)

Primary Examiner—Max F. Hindenburg
Assistant Examiner—Patricia C. Mallari
(74) Attorney, Agent, or Firm—Cooley Godward LLP

(57) ABSTRACT

An indirect calorimeter for measuring the metabolic rate of a subject includes a respiratory connector configured to be supported in contact with the subject so as to pass inhaled and exhaled gases as the subject breathes, a flow pathway, and a hygiene barrier positioned to block a predetermined pathogen from the exhaled gases. The indirect calorimeter also includes a flow pathway having a first end in fluid communication with the respiratory connector and a second end in fluid communication with a source and sink for respiratory gases. The flow pathway includes a flow tube through which the inhaled and exhaled gases pass, an outer housing surrounding the flow tube, and a chamber disposed between the flow tube and the first end. The indirect calorimeter also includes a flow meter configured to generate electrical signals as a function of the instantaneous flow volume of inhaled and exhaled gases passing through the flow pathway, and a component gas concentration sensor operable to generate electrical signals as a function of the instantaneous fraction of a predetermined component gas in the exhaled gases as the gases pass through the flow pathway. The indirect calorimeter further includes a computation unit operable to receive the electrical signals from the flow meter and the concentration sensor and operative to calculate at least one respiratory parameter for the subject as the subject breathes through the calorimeter.

62 Claims, 16 Drawing Sheets

U.S. PATENT DOCUMENTS

| | | | |
|---|---|---|---|
| 2,630,798 A | 3/1953 | White et al. ............... 128/2.07 |
| 2,826,912 A | 4/1958 | Kritz .......................... 73/194 |
| 2,831,348 A | 4/1958 | Kritz ...................... 73/861.28 |
| 2,838,399 A | 6/1958 | Vogel, Jr. ...................... 99/48 |
| 2,869,357 A | 1/1959 | Kritz ............................ 73/32 |
| 2,911,825 A | 11/1959 | Kritz .......................... 73/194 |
| 2,920,012 A | 1/1960 | Sanders et al. ............ 167/51.5 |
| 3,212,684 A | 10/1965 | Seaton et al. ................ 73/190 |
| 3,213,684 A | 10/1965 | Seaton et al. ................ 374/36 |
| 3,220,255 A | 11/1965 | Scranton et al. ............. 73/204 |
| 3,250,270 A | 5/1966 | Bloom ...................... 128/2.07 |
| 3,306,283 A | 2/1967 | Arp ........................... 128/2.07 |
| 3,357,426 A | 12/1967 | Cohen ....................... 128/205 |
| 3,523,529 A | 8/1970 | Kissen ..................... 128/2.07 |
| 3,527,205 A | 9/1970 | Jones ........................ 128/2.08 |
| 3,681,197 A | 8/1972 | Smith .......................... 195/63 |
| 3,725,658 A * | 4/1973 | Stanley et al. .............. 250/364 |
| 3,726,270 A | 4/1973 | Griffis et al. .............. 128/2.08 |
| 3,799,149 A | 3/1974 | Rummel et al. ........... 128/2.07 |
| 3,814,091 A | 6/1974 | Henkin ....................... 128/188 |
| 3,834,375 A | 9/1974 | Sanctuary et al. ......... 128/2.07 |
| 3,895,630 A | 7/1975 | Bachman ................... 128/2.07 |
| 3,902,485 A | 9/1975 | Wallace ................... 128/142.6 |
| 3,938,551 A | 2/1976 | Henkin ....................... 137/613 |
| 3,962,917 A | 6/1976 | Terada ......................... 73/204 |
| 3,979,480 A | 9/1976 | Radici et al. ............ 260/857 F |
| 3,980,080 A | 9/1976 | Muto ...................... 128/146.6 |
| 4,003,396 A | 1/1977 | Fleischmann ................ 137/83 |
| 4,051,847 A | 10/1977 | Henkin ................... 128/145.6 |
| 4,078,554 A | 3/1978 | Lemaitre et al. .......... 128/2.08 |
| 4,186,735 A | 2/1980 | Henneman et al. .... 128/201.25 |
| 4,188,946 A | 2/1980 | Watson et al. ......... 128/204.22 |
| 4,197,857 A | 4/1980 | Osborn ....................... 600/531 |
| 4,200,094 A | 4/1980 | Gedeon et al. ........ 128/201.13 |
| 4,201,205 A | 5/1980 | Bartholomew ......... 128/205.25 |
| 4,211,239 A | 7/1980 | Raemer et al. ............. 128/716 |
| 4,221,224 A | 9/1980 | Clark ......................... 128/718 |
| 4,230,108 A | 10/1980 | Young | |
| 4,233,842 A * | 11/1980 | Raemer et al. .......... 73/861.04 |
| 4,273,119 A | 6/1981 | Marchello .............. 128/201.13 |
| 4,326,514 A | 4/1982 | Eian ...................... 128/202.22 |
| 4,328,797 A | 5/1982 | Rollins, III et al. .... 128/202.27 |
| 4,341,867 A | 7/1982 | Johansen .................... 435/189 |
| 4,359,057 A | 11/1982 | Manzella .................... 128/718 |
| 4,368,740 A * | 1/1983 | Binder ....................... 600/531 |
| 4,386,604 A | 6/1983 | Hershey ..................... 128/718 |
| RE31,424 E | 10/1983 | Ernsting et al. ........ 128/201.18 |
| 4,425,805 A * | 1/1984 | Ogura et al. ............. 73/861.29 |
| 4,440,177 A | 4/1984 | Anderson et al. ........... 600/532 |
| 4,444,201 A | 4/1984 | Itoh ........................... 128/716 |
| 4,454,880 A | 6/1984 | Muto et al. ............. 128/205.25 |
| 4,463,764 A | 8/1984 | Anderson et al. ........... 600/532 |
| 4,488,547 A | 12/1984 | Mason .................. 128/202.22 |
| 4,572,208 A | 2/1986 | Cutler et al. ................ 128/718 |
| 4,582,054 A | 4/1986 | Ferrer .................... 128/200.23 |
| 4,598,700 A | 7/1986 | Tamm ........................ 128/671 |
| 4,608,995 A | 9/1986 | Linnarsson et al. ......... 128/713 |
| 4,619,269 A | 10/1986 | Cutler et al. ................ 128/719 |
| 4,648,396 A | 3/1987 | Raemer ...................... 600/534 |
| 4,658,832 A | 4/1987 | Brugnoli .................... 600/532 |
| 4,691,701 A | 9/1987 | Williams ............... 128/207.14 |
| 4,719,923 A | 1/1988 | Hartwell et al. | |
| 4,728,499 A | 3/1988 | Fehder ........................ 422/56 |
| 4,753,245 A | 6/1988 | Gedeon ...................... 128/718 |
| 4,756,670 A | 7/1988 | Arai ............................. 417/43 |
| 4,781,184 A | 11/1988 | Fife ....................... 128/205.12 |
| 4,796,639 A | 1/1989 | Snow et al. ................ 600/532 |
| 4,799,477 A | 1/1989 | Lewis .................. 128/206.24 |
| D300,272 S | 3/1989 | Rudolph et al. ............... D29/7 |
| D300,273 S | 3/1989 | Rudolph et al. ............... D29/7 |
| D300,274 S | 3/1989 | Rudolph et al. ............... D29/7 |
| D301,774 S | 6/1989 | Rudolph et al. ............... D29/7 |
| 4,850,371 A | 7/1989 | Broadhurst et al. ......... 600/532 |
| 4,856,531 A | 8/1989 | Merilainen ................. 600/532 |
| 4,865,027 A | 9/1989 | Laanen et al. ......... 128/200.21 |
| D305,165 S | 12/1989 | Rudolph et al. ............... D29/7 |
| D306,086 S | 2/1990 | Rudolph et al. ............... D29/7 |
| 4,909,259 A | 3/1990 | Tehrani ...................... 600/531 |
| 4,914,959 A | 4/1990 | Mylvaganam et al. ... 73/861.28 |
| 4,917,108 A | 4/1990 | Mault .......................... 128/718 |
| 4,938,209 A | 7/1990 | Fry ........................ 128/200.21 |
| 4,945,918 A | 8/1990 | Abernathy .................. 600/532 |
| 4,955,946 A | 9/1990 | Mount et al. ............... 600/532 |
| 4,986,268 A | 1/1991 | Tehrani ...................... 128/204 |
| 4,994,117 A | 2/1991 | Fehder ........................ 436/133 |
| 4,998,018 A | 3/1991 | Kurahashi et al. .......... 250/343 |
| 5,005,572 A | 4/1991 | Raemer et al. ......... 128/207.14 |
| 5,012,805 A | 5/1991 | Muckerheide ......... 128/205.28 |
| 5,022,406 A | 6/1991 | Tomlinson ................. 128/718 |
| 5,038,773 A | 8/1991 | Norlien et al. .......... 128/205.23 |
| 5,038,792 A | 8/1991 | Mault ......................... 128/718 |
| 5,042,500 A | 8/1991 | Norlien et al. .............. 600/532 |
| 5,042,501 A | 8/1991 | Kenny et al. | |
| 5,060,506 A | 10/1991 | Douglas ...................... 73/24.1 |
| 5,060,655 A | 10/1991 | Rudolph ..................... 128/716 |
| 5,060,656 A | 10/1991 | Howard ...................... 128/718 |
| 5,067,492 A | 11/1991 | Yelderman et al. ......... 600/532 |
| 5,069,220 A | 12/1991 | Casparie et al. ............. 218/719 |
| 5,072,737 A | 12/1991 | Goulding ................... 128/718 |
| 5,081,871 A | 1/1992 | Glaser ..................... 73/863.23 |
| 5,095,900 A | 3/1992 | Fertig et al. ............ 128/207.14 |
| 5,095,913 A | 3/1992 | Yelderman et al. ......... 128/719 |
| 5,117,674 A | 6/1992 | Howard ...................... 73/31.07 |
| 5,119,825 A | 6/1992 | Huhn .......................... 600/529 |
| 5,178,155 A * | 1/1993 | Mault ......................... 600/531 |
| 5,179,002 A | 1/1993 | Fehder ......................... 435/25 |
| 5,179,958 A * | 1/1993 | Mault ......................... 600/531 |
| 5,197,464 A | 3/1993 | Babb et al. ............. 128/207.14 |
| D334,633 S | 4/1993 | Rudolph ........................ D29/7 |
| 5,214,966 A | 6/1993 | Delsing .................... 73/861.28 |
| 5,233,996 A | 8/1993 | Coleman et al. ............ 600/529 |
| 5,235,972 A | 8/1993 | Strong ................... 128/206.21 |
| 5,265,595 A | 11/1993 | Rudolph .................. 128/204.18 |
| 5,279,289 A | 1/1994 | Kirk ....................... 128/205.23 |
| 5,282,473 A | 2/1994 | Braig et al. ................. 600/532 |
| 5,285,794 A | 2/1994 | Lynch ........................ 128/719 |
| 5,293,875 A | 3/1994 | Stone ......................... 128/719 |
| 5,297,544 A | 3/1994 | May et al. ............. 128/202.22 |
| 5,299,579 A | 4/1994 | Gedeon et al. .............. 600/532 |
| 5,303,712 A | 4/1994 | Van Duren ................. 600/529 |
| 5,309,921 A | 5/1994 | Kisner et al. ............... 600/532 |
| 5,326,973 A | 7/1994 | Eckerbom et al. .......... 250/343 |
| 5,337,739 A * | 8/1994 | Lehman ............... 128/205.274 |
| 5,353,789 A | 10/1994 | Schlobohm ............ 128/206.24 |
| 5,355,879 A | 10/1994 | Brain | |
| 5,357,945 A | 10/1994 | Messina ................. 128/200.14 |
| 5,357,972 A | 10/1994 | Norlien ...................... 128/725 |
| 5,363,857 A | 11/1994 | Howard ...................... 600/531 |
| 5,375,592 A | 12/1994 | Kirk et al. .............. 128/207.14 |
| 5,386,825 A | 2/1995 | Bates ..................... 128/205.27 |
| 5,398,695 A | 3/1995 | Anderson et al. ........... 600/532 |
| 5,400,781 A | 3/1995 | Davenport ............. 128/206.28 |
| 5,402,796 A | 4/1995 | Packer et al. ............... 128/719 |
| 5,419,326 A | 5/1995 | Harnoncourt .......... 128/660.02 |
| 5,425,374 A | 6/1995 | Ueda et al. .................. 600/532 |
| 5,450,193 A | 9/1995 | Carlsen et al. .............. 356/301 |
| 5,454,369 A | 10/1995 | Müller et al. ............ 128/206.24 |
| 5,464,982 A | 11/1995 | Drucker et al. ............. 250/343 |
| 5,468,451 A | 11/1995 | Gedeon ........................ 422/58 |
| 5,468,961 A | 11/1995 | Gradon et al. .............. 250/345 |
| 5,480,611 A | 1/1996 | Mills et al. ................... 422/55 |

| | | | |
|---|---|---|---|
| 5,503,151 A | 4/1996 | Harnoncourt et al. | 128/660.02 |
| 5,513,648 A | 5/1996 | Jackson | |
| 5,533,512 A | 7/1996 | Novotny et al. | 600/532 |
| 5,538,000 A | 7/1996 | Rudolph | 128/205.25 |
| 5,545,897 A | 8/1996 | Jack | 250/339.13 |
| 5,570,697 A | 11/1996 | Walker et al. | 128/719 |
| 5,590,644 A * | 1/1997 | Rosenkoetter | 128/201.13 |
| 5,603,317 A | 2/1997 | Farmer | 128/205.27 |
| 5,632,281 A | 5/1997 | Rayburn | 128/719 |
| 5,645,071 A | 7/1997 | Harnoncourt et al. | 128/719 |
| 5,647,370 A | 7/1997 | Harnoncourt | 128/725 |
| 5,676,132 A | 10/1997 | Tillotson et al. | 128/204.23 |
| 5,676,133 A * | 10/1997 | Hickle et al. | 128/205.12 |
| D385,960 S | 11/1997 | Rudolph | D24/110.4 |
| 5,705,735 A | 1/1998 | Acorn | 73/23.3 |
| 5,724,964 A * | 3/1998 | Brunson et al. | 128/206.19 |
| 5,754,288 A | 5/1998 | Yamamoto et al. | 356/301 |
| 5,758,642 A | 6/1998 | Choi | 128/206.21 |
| 5,765,553 A | 6/1998 | Richards et al. | 128/203.29 |
| 5,771,885 A | 6/1998 | Putrello | 128/205.27 |
| 5,782,234 A | 7/1998 | Bates | 128/205.27 |
| 5,789,660 A | 8/1998 | Kofoed et al. | 73/232 |
| 5,796,009 A | 8/1998 | Delsing | 73/861.28 |
| 5,800,360 A | 9/1998 | Kisner et al. | 600/532 |
| 5,816,246 A | 10/1998 | Mirza | 128/726 |
| 5,831,175 A | 11/1998 | Fletcher-Haynes | 73/861.28 |
| 5,834,626 A | 11/1998 | De Castro et al. | 73/23.3 |
| 5,836,300 A | 11/1998 | Mault | 600/532 |
| 5,841,021 A | 11/1998 | De Castro et al. | 73/23.2 |
| 5,857,460 A | 1/1999 | Popitz | 128/206.21 |
| 5,922,610 A | 7/1999 | Alving et al. | 436/116 |
| 5,932,812 A | 8/1999 | Delsing | 73/861.02 |
| 5,957,858 A | 9/1999 | Micheels et al. | 600/532 |
| 5,965,061 A | 10/1999 | Larsson et al. | 252/408.1 |
| 5,992,413 A | 11/1999 | Martin, Jr. et al. | 128/201.13 |
| 6,010,459 A | 1/2000 | Solkoff et al. | 600/532 |
| 6,017,315 A * | 1/2000 | Starr et al. | 600/538 |
| 6,044,843 A | 4/2000 | O'Neil et al. | 128/204.23 |
| 6,055,982 A * | 5/2000 | Brunson et al. | 128/206.12 |
| 6,082,360 A | 7/2000 | Rudolph et al. | 128/206.25 |
| 6,095,986 A | 8/2000 | Braig et al. | 600/532 |
| 6,099,481 A | 8/2000 | Daniels et al. | 600/538 |
| 6,120,784 A | 9/2000 | Snyder, Jr. | 424/404 |
| 6,135,107 A | 10/2000 | Mault | 128/204.23 |
| 6,173,712 B1 | 1/2001 | Brunson | 128/206.19 |
| 6,190,327 B1 | 2/2001 | Isaacson et al. | 600/529 |
| 6,191,421 B1 | 2/2001 | Yamamori et al. | 250/343 |
| 6,192,886 B1 | 2/2001 | Rudolph | 128/207.13 |
| 6,197,577 B1 | 3/2001 | Jeffrey et al. | 435/288.7 |
| 6,199,550 B1 | 3/2001 | Wiesmann et al. | 128/204.23 |
| 6,206,837 B1 | 3/2001 | Brugnoli | 600/529 |
| 6,341,606 B1 | 1/2002 | Bordewick et al. | 128/206.25 |
| 6,402,698 B1 * | 6/2002 | Mault | 600/532 |
| 6,468,222 B1 * | 10/2002 | Mault et al. | 600/538 |
| 6,584,976 B2 * | 7/2003 | Japuntich et al. | 128/206.12 |
| 6,645,158 B2 * | 11/2003 | Mault | 600/532 |
| 2001/0016733 A1 | 8/2001 | Frey et al. | 606/5 |
| 2002/0023647 A1 | 2/2002 | Hansen et al. | 128/205.25 |
| 2002/0026943 A1 | 3/2002 | Castiglione | 128/206.19 |
| 2004/0199083 A1 * | 10/2004 | Mault | 600/532 |

FOREIGN PATENT DOCUMENTS

| | | |
|---|---|---|
| EP | 0 072 229 A1 | 9/1982 |
| EP | 0459647 A | 2/1991 |
| EP | 0 712 638 | 12/1995 |
| GB | 2 092 009 A | 1/1981 |
| GB | 2323292 | 9/1998 |
| WO | WO 90/01698 | 2/1990 |
| WO | WO 94/02190 | 2/1994 |
| WO | WO 96/40340 | 12/1996 |

OTHER PUBLICATIONS

British Journal of Anaesthesia, vol. 49, 1977 London (GB) pp. 575–587, J.A. Bushman et al. "Closed Circuit Anaesthesia".

IEEE Transactions On Biomedical Engineering, vol. 35, No. 9, Sep. 1988, pp. 653–659, Capek et al., "Noninvasive Measurement of Cardiac Output Using Partial CO2 ReBreathing".

Clinics In Chest Medicine (Review), vol. 10, 1989, pp. 255–264, Heigenhauser et al., "Measurement of Cardiac Output by Carbon Dioxide ReBreathing Methods".

* cited by examiner

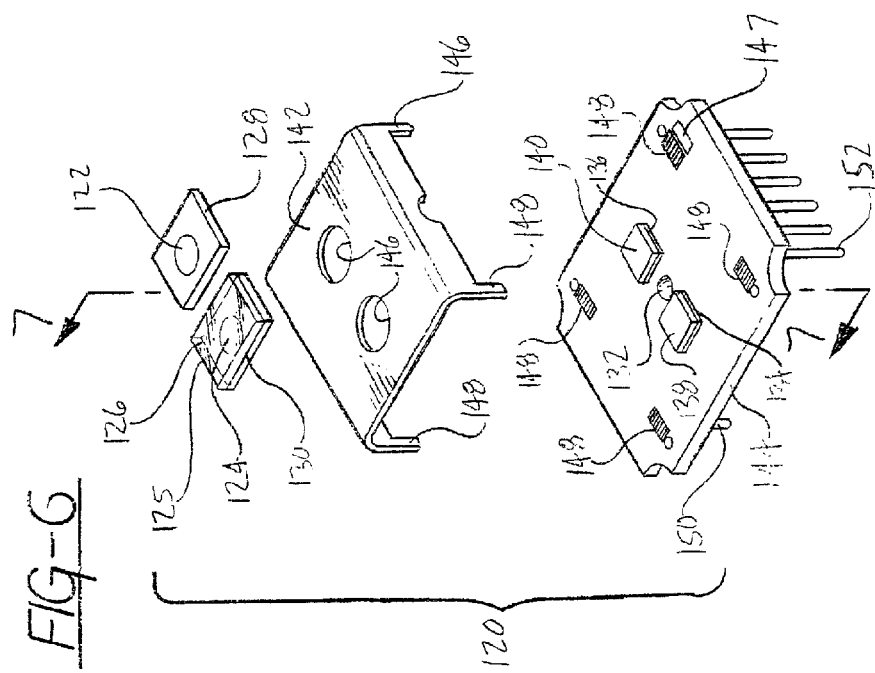
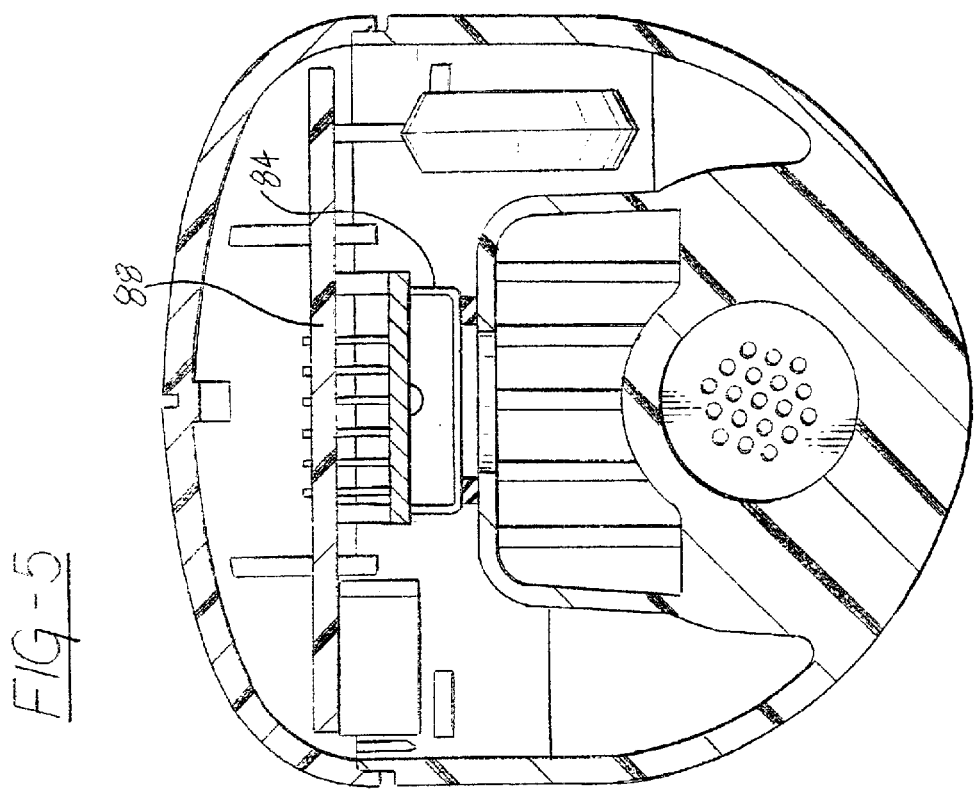

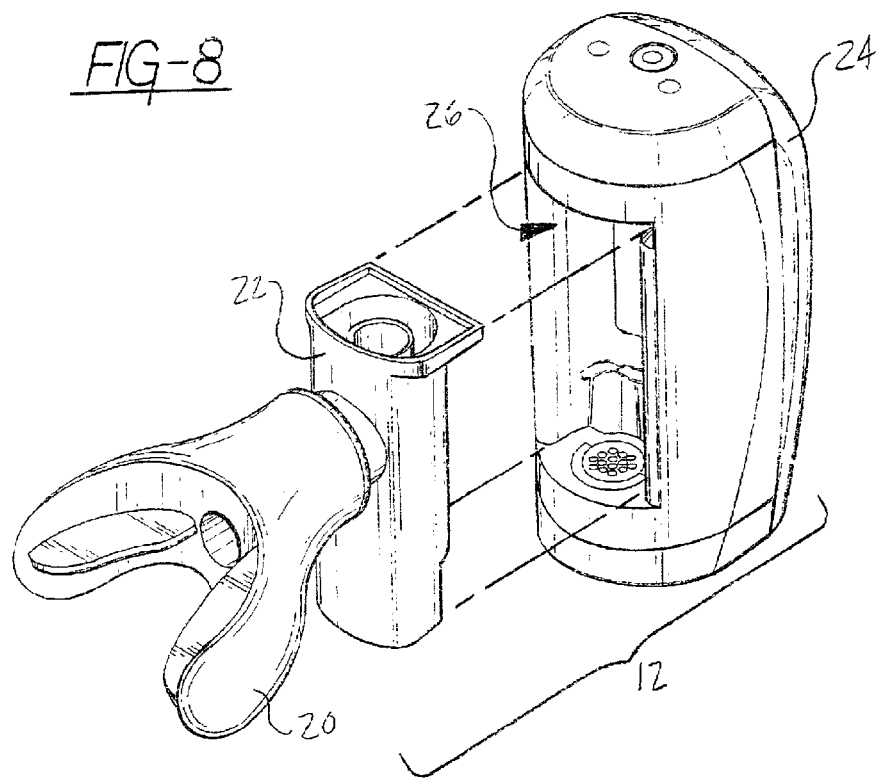
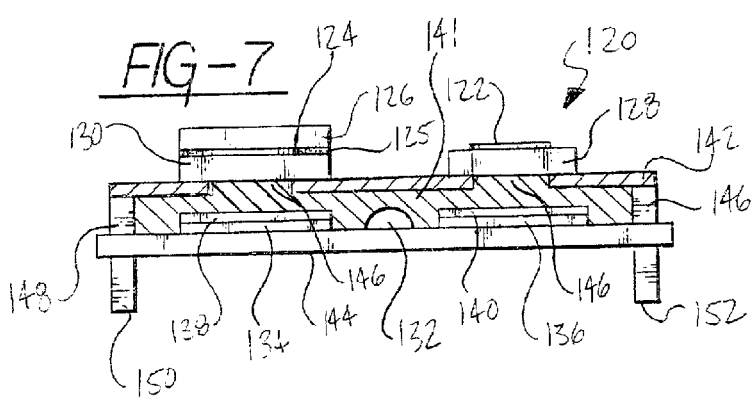
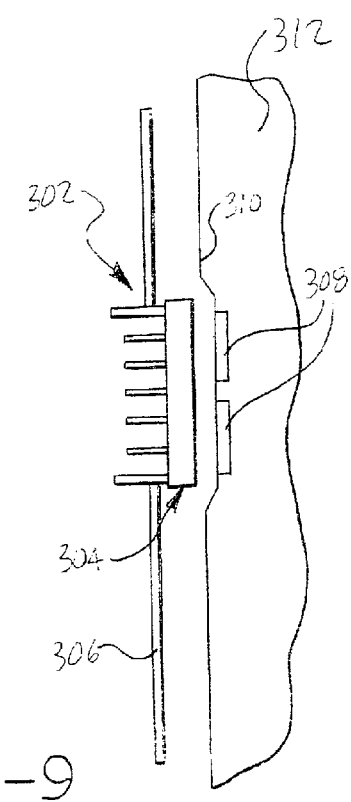

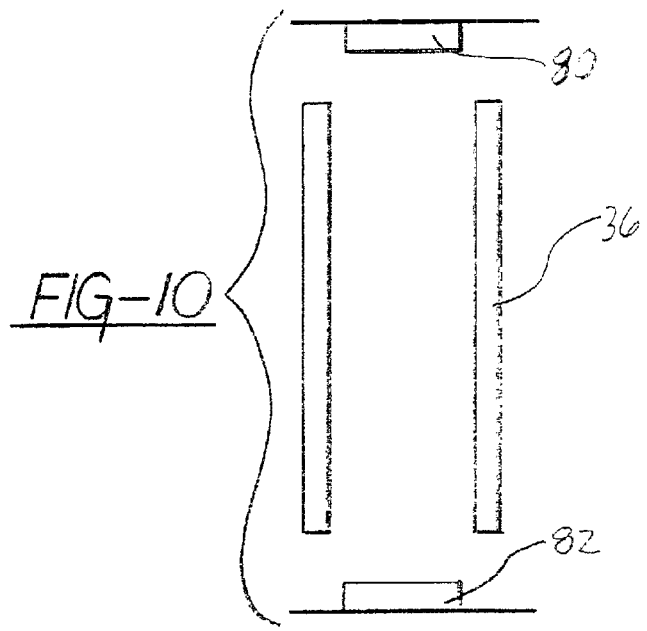
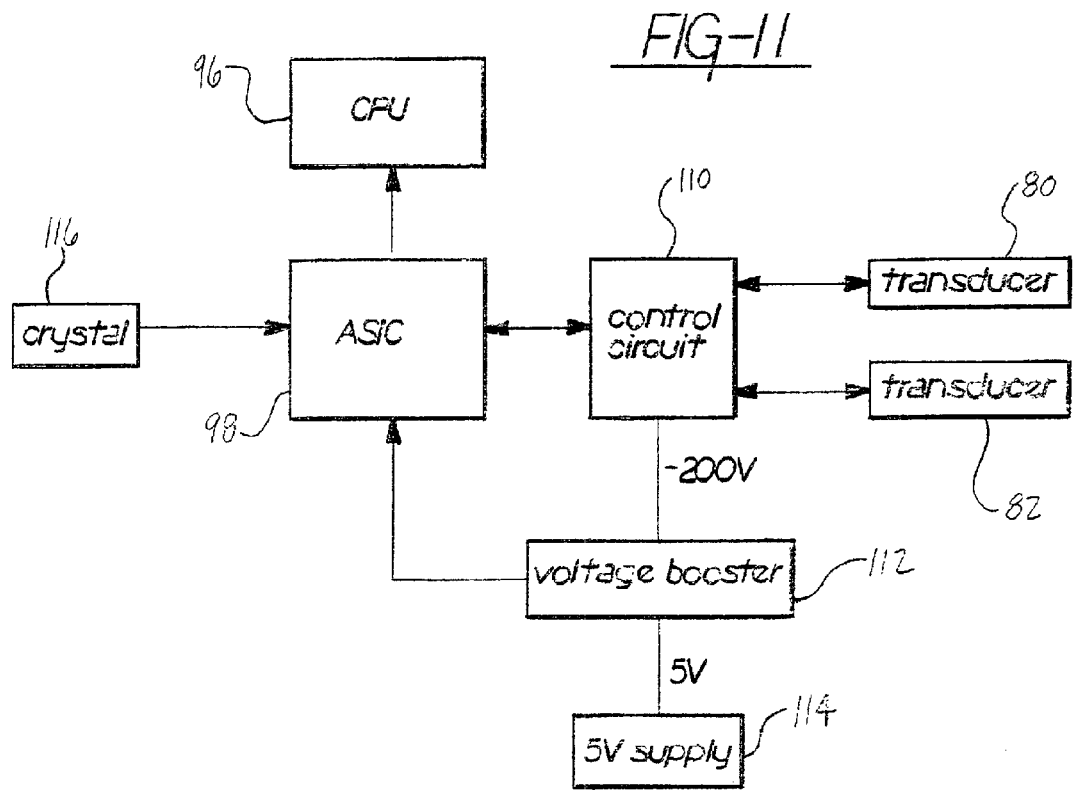

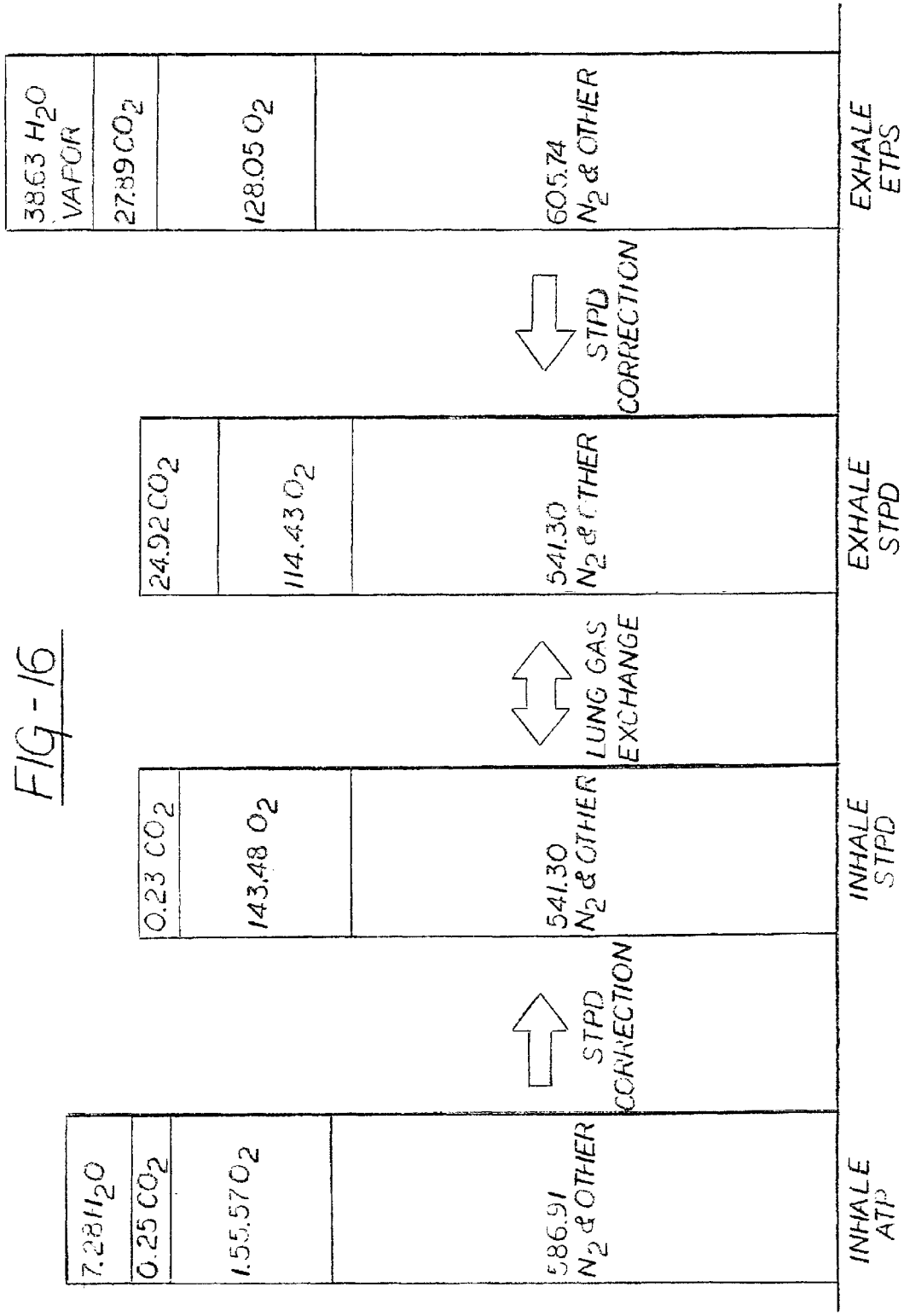

METABOLIC CALORIMETER EMPLOYING RESPIRATORY GAS ANALYSIS

REFERENCE TO RELATED APPLICATIONS

This application is a continuation of U.S. patent application Ser. No. 09/630,398 filed Aug. 2, 2000 now U.S. Pat. No. 6,468,222, which claims priority from U.S. provisional patent application Ser. Nos. 60/146,898, filed Aug. 2, 1999; 60/155,035, filed Sep. 20, 1999; 60/219,241, filed Jul. 18, 2000; and 60/218,863, filed Jul. 18, 2000, the entire contents of all are incorporated herein by reference.

FIELD OF THE INVENTION

This invention relates to a respiratory instrument with improved sanitation for measuring metabolism and related respiratory parameters by indirect calorimetry.

BACKGROUND OF THE INVENTION

U.S. Pat. Nos. 4,917,108; 5,038,792; 5,178,155; 5,179,958; and 5,836,300, all to Mault, a coinventor of the present application, are incorporated herein by reference. These patents disclose systems for measuring metabolism and related respiratory parameters through indirect calorimetry. These instruments generally employ flow meters which pass both the inhalations and the exhalations of a user breathing through the instrument and integrate the resulting instantaneous flow signals to determine total full flow volumes. In one embodiment, the exhaled gases generated by the user are passed through a carbon dioxide scrubber before passing through the flow meter so that the differences between the inhaled and exhaled volumes is essentially a measurement of the oxygen consumed by the lungs. In an alternative embodiment, the concentration of carbon dioxide exhaled by the user is determined by passing the exhaled volume through a capnometer and integrating that signal with the exhaled flow volume. The oxygen consumption can then be calculated as the difference between the inhaled and exhaled volumes minus the exhaled carbon dioxide volume.

The scrubber used with certain of these systems was relatively bulky and required replenishment after extended usage. The capnometers used with the instruments to measure carbon dioxide concentration had to be highly precise and accordingly expensive because any error in measurement of the carbon dioxide content of the exhalation produces a substantially higher error in the resulting determination of the oxygen content of the exhalation.

Additional approaches to indirect calorimetry and cardiac output monitoring are disclosed in Mault's co-pending applications Ser. Nos. 09/008,435; 09/191,782; PCT/US99/02448; PCT/US99/17553; PCT/US99/27297; PCT/US00/12745, each of which are incorporated herein by reference.

SUMMARY OF THE INVENTION

The present invention provides an indirect calorimeter for measuring the metabolic rate of a subject. The calorimeter includes a respiratory connector configured to be supported in contact with the subject so as to pass inhaled and exhaled gases as the subject breathes, a flow pathway operable to receive and pass inhaled and exhaled gases, and a hygiene barrier positioned to block a predetermined pathogen from the exhaled gases. A first end of the flow pathway is in fluid communication with the respiratory connector and a second end is in fluid communication with a source and sink for respiratory gases which may be either the ambient atmosphere, a mechanical ventilator, or other gas mixture source. A flow meter generates electrical signals as a function of the instantaneous flow volume of inhaled and exhaled gases passing through the flow pathway. A component gas concentration sensor generates electrical signals as a function of the instantaneous fraction of a predetermined component gas in the inhaled and/or exhaled gases as the gases pass through the flow pathway. A computation unit receives the electrical signals from the flow meter and the component gas concentration sensor and calculates at least one respiratory parameter for the subject as the subject breathes through the calorimeter.

In some embodiments, the flow pathway includes a flow tube through which the inhaled and exhaled gases pass and a chamber disposed between the first end of the pathway and the flow tube. The chamber surrounds one end of the flow tube and forms a concentric chamber.

In other embodiments, a flow tube forms part of the flow pathway and is disposed between the two ends of the pathway. The first end of the pathway takes the form of an inlet conduit that extends perpendicularly to the flow tube.

In some embodiments, the flow pathway includes an elongated flow tube through which inhalation and exhalation gases pass. The flow meter is an ultrasonic flow meter and includes two spaced apart ultrasonic transducers. The transducers are each aligned with the elongated flow tube such that ultrasonic pulses transmitted between the transducers travel in a path that is generally parallel to the flow of fluid in the flow tube.

Yet other embodiments of the present invention are also disclosed in the following description and the accompanying figures.

BRIEF DESCRIPTION OF THE DRAWINGS

Other advantages and applications of the present invention will be made apparent by the following detailed description of preferred embodiments of the invention. The description makes reference to the accompany drawings in which:

FIG. 5 is a cross sectional view of the first embodiment of the invention, taken along lines 5—5 in FIG. 4;

FIG. 6 is a perspective view in exploded form of one embodiment of an oxygen sensor for use with the present invention;

FIG. 7 is a cross sectional view of an assembled oxygen sensor for use with the present invention;

FIG. 8 is a perspective view of the present invention with an alternative mouthpiece, shown with the disposable portion removed from the reusable portion;

FIG. 9 is a cross sectional view of an alternative approach to constructing an oxygen sensor for use with the present invention;

FIG. 10 is a diagram showing the general configuration of a flow tube and ultrasonic sensors according to the present invention;

FIG. 11 is a schematic showing the electronic circuitry for use with an embodiment of an ultrasonic flow sensing system that may be used with the present invention;

FIG. 16 is a bar graph showing an example gas exchange for a single inhalation and exhalation;

DETAILED DESCRIPTION OF THE INVENTION

Basic Configuration of Calorimeter

Figure 1:
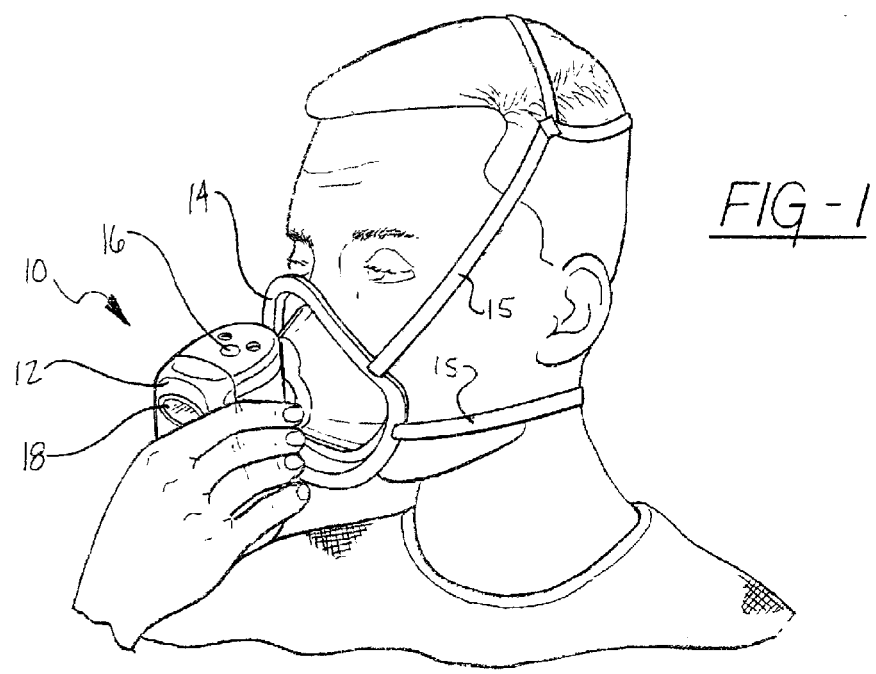
FIG. 1 is a perspective view of a respiratory calorimeter according to a first embodiment of the present invention with the calorimeter shown being used by a user.
Figure 2:
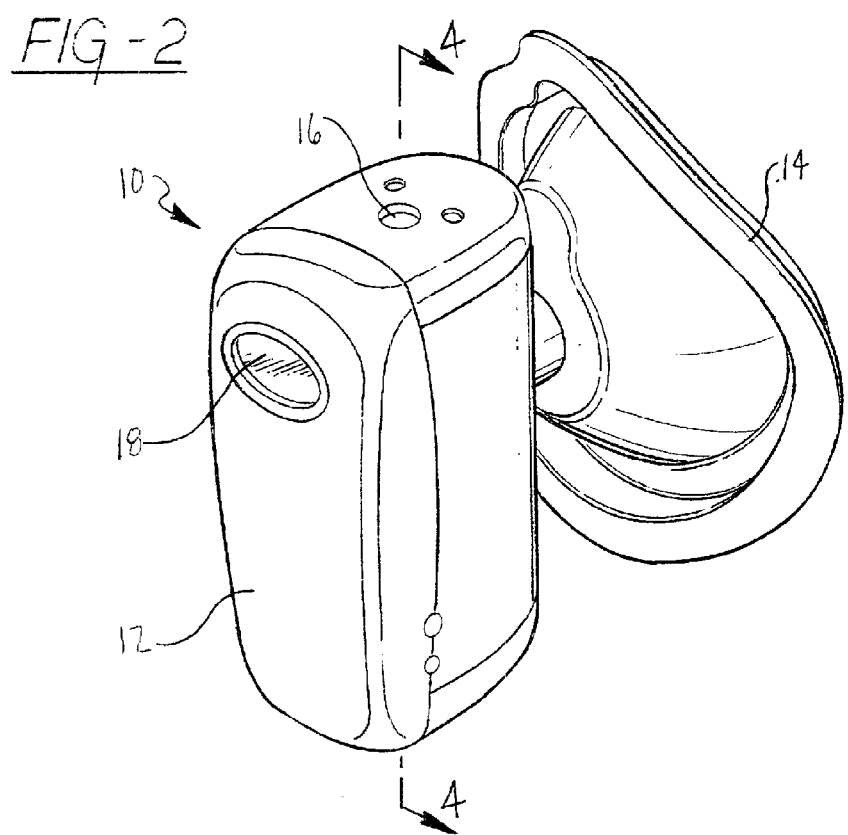
FIG. 2 is a perspective view of the first embodiment of the invention.

Referring to FIGS. 1 and 2, a respiratory calorimeter according to the present invention is generally shown at 10. The calorimeter 10 includes a body 12 and a respiratory connector, such as mask 14, extending from the body 12. In use, the body 12 is grasped in the hand of a user and the mask 14 is brought into contact with the user's face so as to surround their mouth and nose, as best shown in FIG. 1. An optional pair of straps 15 is also shown in FIG. 1. The straps provide an alternative to holding the body 12 of the calorimeter 10 with a hand. Instead, the straps can support the mask and calorimeter in contact with the user's face.

With the mask 14 in contact with their face, the user breathes normally through the calorimeter 10 for a period of time. The calorimeter 10 measures a variety of factors and calculates one or more respiratory parameters, such as oxygen consumption and metabolic rate. A power button 16 is located on the top side of the calorimeter 10 and allows the user to control the calorimeter's functions. A separate light is located below the power button 16, with the power button 16 acting as a light pipe so that the button appears illuminated when the light is on. The light is preferably used to indicate the status of the calorimeter before, during, and after a test. A display screen is disposed behind lens 18 on the side of the calorimeter body 12 opposite the mask 14. Test results are displayed on the screen following a test.

Referring now to FIG. 8, a calorimeter with an alternative respiratory connector, a mouthpiece 20 rather than the mask 14 of FIG. 1, is shown. The mouthpiece 20 is preferably sized and shaped so that it may be easily inserted into a user's mouth and respiration passes through it. The mouthpiece may be made from a variety of materials, including silicone. Depending on user preference, a calorimeter according to the present invention may be used with either a mask or a mouthpiece. A mouthpiece 20 may be required for certain users, such as users with facial hair. For accurate results, it is necessary that substantially all of the user's inhalations and exhalations pass through the calorimeter. Therefore, when a mouthpiece 20 is used as a respiratory connector, it is preferred that a nose clip, not shown, be used to seal off the user's nostrils.

As best shown in FIG. 8, the body 12 of the calorimeter preferably includes a disposable flow tube portion 22 and a reusable main portion 24. The respiratory connector, such as mouthpiece 20, connects to the side of the disposable flow tube portion 22. In use, each user is given a fresh disposable portion 22 along with the appropriate respiratory connector 14 or 20. The reusable main portion may be used with multiple users. The reusable main portion 24 has a recess 26 defined in one side and shaped so as to accept the disposable portion 22.

Basic Mechanical Configuration

Figure 3:
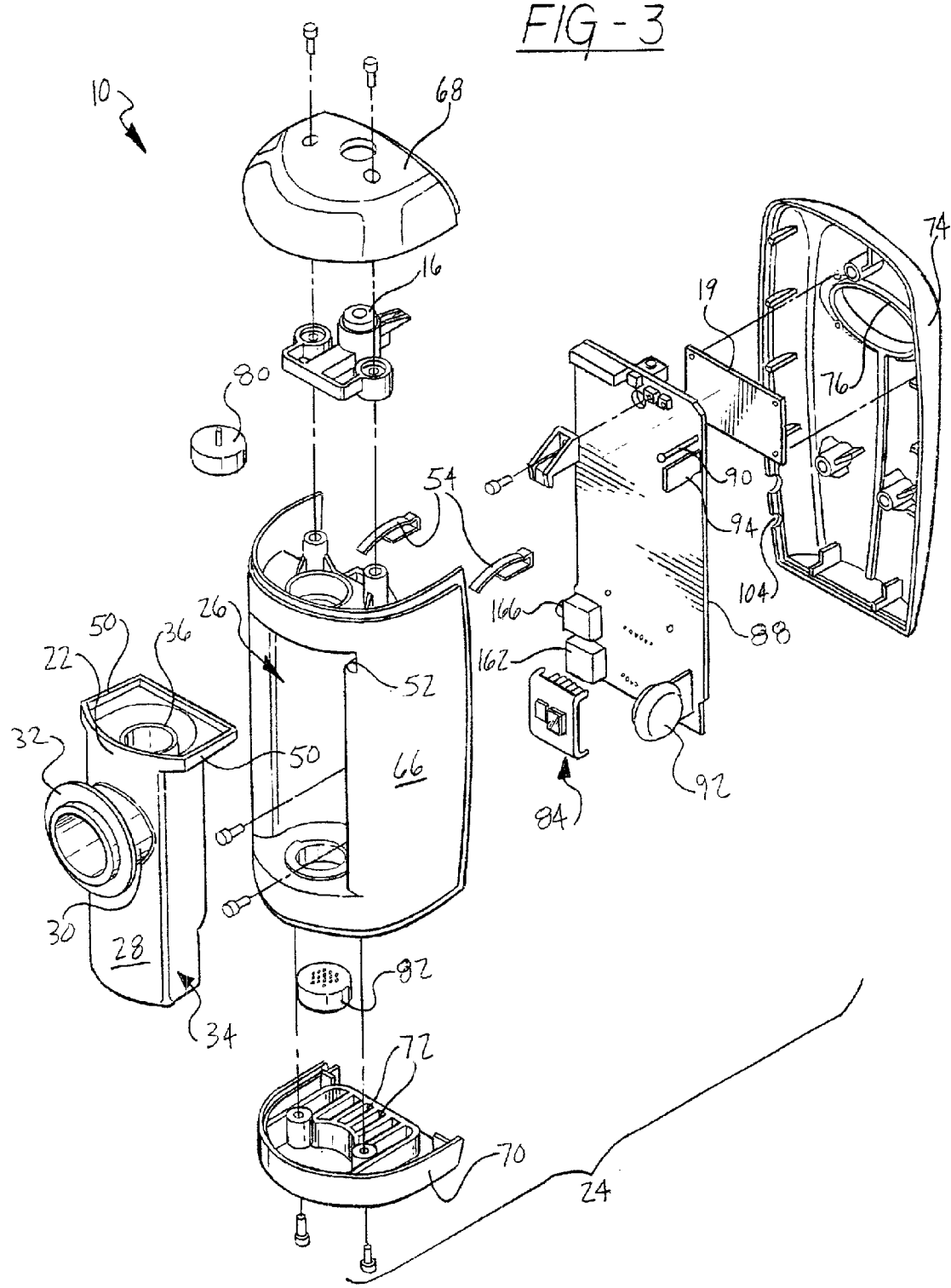
FIG. 3 is a perspective view in exploded form of the first embodiment of the invention.
Figure 4:
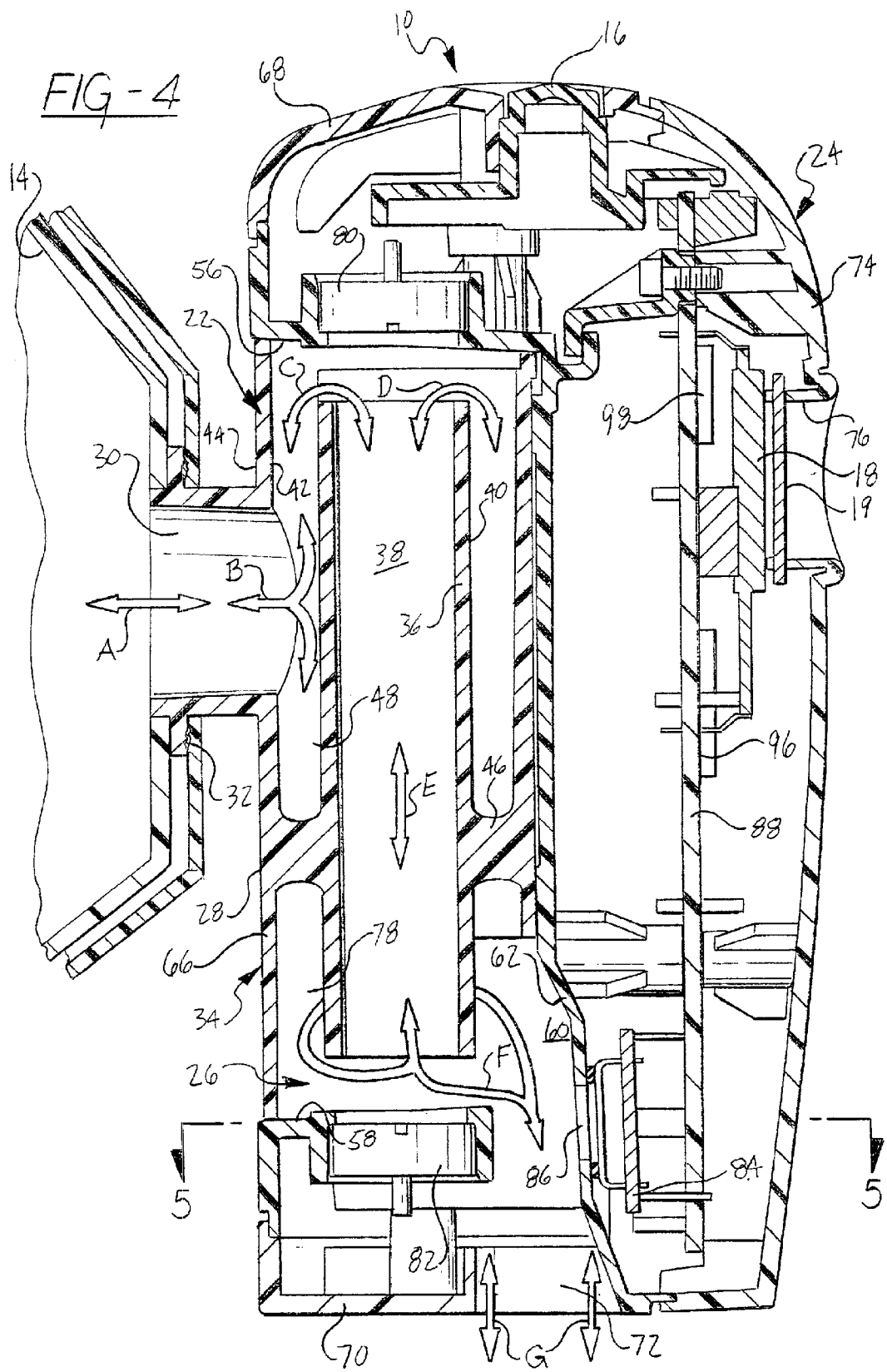
FIG. 4 is a cross sectional view of the first embodiment of the invention, taken along lines 4—4 in FIG. 2.

Referring now to FIGS. 3 and 4, the mechanical configuration of the calorimeter 10 will be described in more detail. FIG. 3 illustrates all components of the calorimeter in exploded form, with the disposable portion 22 removed from the recess 26 in the main portion 24. FIG. 4 is a vertical cross section of the assembled calorimeter with the disposable portion 22 docked in the main portion. Orientations such as vertical and horizontal are used throughout this specification. However, it should be understood that these orientation descriptors are used merely for convenience and are arbitrary since the calorimeter could be described in other positions.

The disposable portion 22 of the calorimeter 10 is generally elongated in the vertical direction and may be said to have a generally vertical outward face 28 which remains exposed when the disposable portion 22 is received in the recess 26. In the preferred embodiment, the outward face has a height of about 75 mm and a width of about 28 mm. An inlet conduit 30 extends perpendicularly outwardly from this outward face 28. In the preferred embodiment, the conduit 30 extends about 2 mm from the outward face 28 and has an internal diameter of about 19 mm. A radial attachment flange 32 is provided adjacent the outer end of the inlet conduit 30 and provides for attachment of a respiratory connector, such as mask 14, as best shown in FIG. 4. The respiratory connector is preferably securely attached and sealed to the attachment flange 32 such as by sonic welding.

The disposable portion 22 generally consists of an outer shell 34 with generally vertical side walls and a vertical flow tube 36 within the shell 34. The flow tube 36 is preferably cylindrical with open upper and lower ends. In the preferred embodiment, the flow tube has a length of about 63 mm and an internal diameter of about 12 mm. For definitional purposes, the flow tube 36 maybe said to have an inner surface 38 on the inside of the tube 36 and an outer surface 40 on the outside of the tube 36. Likewise, the outer shell 34 may be said to have an inner surface 42 inside the shell and an outer surface 44 outside the shell. As best shown in FIG. 4, the outer surface 40 of the flow tube 36 is spaced from the inner surface 42 of the outer shell 34 so as to define a concentric gap between these two components of the disposable portion 22. The gap varies in width somewhat at different positions around the tube. However, the gap is generally at least 5 mm in width at the top of the flow tube 36, with the outer surface 40 of the tube 36 and the inner surface 42 of the shell 34 drafting toward each other slightly, for molding purposes, as the gap extends downwardly.

The flow tube 36 and the outer shell 34 are interconnected by an annular flange 46 which extends between the inner surface 42 of the outer shell 34 and the outer surface 40 of the flow tube 36. The annular flange 46 interconnects the flow tube 36 and outer shell 34 and is positioned closer to the bottom of the flow tube 36 than to the top. In the preferred embodiment, the flange 46 is positioned about 43 mm from the top of the tube 36. The flange 46 completely seals the outer surface 40 of the flow tube 36 to the inner surface 42 of the outer shell 34 so as to define a concentric chamber 48 above the flange 46 and between the outer surface 40 of the flow tube 36 and inner surface 42 of the outer shell 34.

As best shown in FIG. 4, the inlet conduit 30 is in fluid communication with the concentric chamber 48 as it intersects and penetrates the outward face 28 of the outer shell 34 above the flange 46. In the preferred embodiment, the center of the inlet conduit 30 is about 25 mm from the top of the outward face.

Referring again to FIG. 3, the upper end of the outer shell 34 of the disposable 22 has a pair of sidewardly projecting, generally horizontal, engagement rails 50. The recess 26 in the reusable portion 24 of the calorimeter has a pair of corresponding engagement slots 52, only one of which is shown. When the disposable portion 22 docks into the recess 26 of the reusable portion 24, the engagement rails 50 slide into the engagement slots 52 to securely interconnect the disposable portion and the remainder of the calorimeter 10. Springs 54 form part of the engagement slots 52 and push upwardly on the underside of the engagement rails 50. As will be clear to those of skill in the art, the disposable portion may be made from a variety of materials. In the preferred embodiment, the disposable is molded from ABS plastic.

According to one embodiment of the present invention, the disposable portion 22 and reusable portion 24 are designed such that only specifically designed authentic disposable portions work with the reusable portion. Various approaches to accomplishing this will be apparent to those of skill in the art. For example, the disposable portion may include an authenticating device such as a chip or magnetic strip that is recognized by the reusable main portion. Preferably, the calorimeter is operable only when an authentic disposable portion is docked in the reusable portion. Also, the main portion may include some type of interlock that physically "recognizes" that a correct disposable is completely docked, so that a test may not be performed with a disposable that is incorrectly or incompletely docked. As a further alternative, the reusable portion may recognize, record, and/or transmit some type of identification code associated with each disposable portion. This allows accurate record keeping. Also, specific codes can be assigned to specific users, allowing the reusable portion to identify particular users based on the disposable portion being docked.

Referring now to both FIGS. 3 and 4, the upper end of the recess 26 in the reusable main portion 34 is defined by an upper wall 56. The upper edge of the outer shell 34 of the disposable portion 22 fits against this upper wall 56 and is held in place by the springs 54. A bottom ledge 58 generally defines the lower end of the recess 26. The lower end of the outer shell 28 of the disposable portion 22 fits against this bottom ledge 58. Therefore, the upper wall 56 of the recess 26 generally seals off the upper end of the outer shell 34 of the disposable portion 22 when the disposable portion is docked with the reusable portion. Alternatively, a seal may be provided on the upper edge of the outer shell 28 or on the upper wall 56 to improve sealing. Preferably, the sides of the disposable portion 22 also fit snugly against the sides of the recess 26. It is preferred that when the disposable portion 22 is docked into the reusable portion, very little or no respiration gases passing through the disposable portion leaks through the joints between the disposable portion 22 and the remainder of the calorimeter 10.

The bottom of the recess 26 is only partially defined by the bottom ledge 58. Behind the ledge 58 is an outlet flow passage 60 defined between the rear edge of the ledge 58 and the rear wall 62 of the recess 26.

The flow tube 36 does not extend as far, either upwardly or downwardly, as the outer shell 34 of the disposable portion 22. The upper end of the flow tube 36 stops short of the upper end of the outer housing and also stops short of the upper wall 56 of the recess 26 when the disposable portion 22 is docked with the reusable portion. In the preferred embodiment, a gap of about 6 mm is left between the upper end of the flow tube and the upper wall 56. Therefore, the inside of the flow tube 36 is in fluid communication with the concentric chamber 48 when the disposable portion 22 is docked in the reusable portion 24. The bottom end of the flow tube 36 also stops short of the bottom ledge 58 of the recess 26. In the preferred embodiment, a gap of about 6 mm is left between the bottom end of the flow tube and the ledge 58. Therefore, the bottom end of the flow tube 36 is not blocked off by the ledge 58 and the inside of the flow tube 36 is in fluid communication with the outlet flow passage 60 behind the ledge 58.

Referring to both FIGS. 3 and 4, the reusable main portion 24 of the calorimeter 10 has an outer housing 64 constructed from multiple pieces. A semi-cylindrical main housing member 66 defines the side walls of the reusable portion and the recess 26. A top cap 68 closes off the top of the main housing member 66 and houses the power button 16. A ventilated bottom cap 70 closes off the bottom of the main housing member 66. The bottom cap 70 includes an open grill 72 which is in fluid communication with the outlet flow passage 60 within the housing. Therefore, respiration gases and atmospheric air can flow between the area outside the calorimeter 10 and the area inside the calorimeter by flowing through the grill 72. A front cap 74 closes off the front of the main housing member 66, with front being defined as the side of the calorimeter facing away from the mask. The front cap 74 houses the lens 19 and has an oval opening 76 defined therein to allow viewing of the display screen 18 behind the lens 19. As shown, the main housing member 66, the top cap 68, the bottom cap 70, and the front cap 74 are interconnected using a variety of fasteners. Alternatively, they can be designed so as to snap together, could be adhesively interconnected, or could be interconnected in other ways. As will be clear to those of skill in the art, the components forming the outer housing 64 may be made from various materials. In the preferred embodiment, the components are molded from ABS plastic.

Flow Path

Referring now to FIG. 4, the flow path for respiration gases through the calorimeter 10 will be described. In use, when a user exhales, their exhalation passes through the respiratory connector, through the calorimeter 10, and out to ambient air. Upon inhalation, ambient air is drawn into and through the calorimeter and through the respiratory connector to the user. This flow of respiratory gases is illustrated by arrows A–G. It should be understood that instead of ambient air, the calorimeter may be connected to a mechanical ventilator, or to an alternative gas supply.

Arrow A indicates flow to and from the user and into and out of the inlet conduit 30. The inlet conduit 30 interconnects with the concentric chamber 48 so that respiration flowing from the inlet conduit 30 encounters the outer surface 40 of the flow tube 36 and must therefore turn either upwardly, downwardly, or around the sides of the outer surface 40 of the flow tube 36, as shown by arrows B. This abrupt change of flow direction has several effects. First, the lower end of the concentric chamber 48 acts as a saliva trap. That is, excess moisture in a user's exhalations will tend to drop out of the exhalation flow and fall to the lower end of the concentric chamber 48. Secondly, the various routes the exhalation gas may take, and the changes of direction, helps to introduce turbulent flow to the flow tube. Turbulent flow through the flow tube 36 is preferred for flow measurement purposes. Most importantly, the concentric chamber 48 serves to introduce the respiration gases to the flow tube 36 from all radial directions as evenly as possible. This helps to allow flow in the flow tube that can be measured linearly across a wider range of flow velocities.

Gas flowing from the concentric chamber during exhalation encounters the upper wall 56 of the recess 26 causing the flow to turn approximately 180°, as shown by arrows C and D, and flow downwardly through the inside of the flow tube 36. Flow through the flow tube 36 is indicated by arrow E. As discussed previously, the bottom end of the flow tube 36 stops short of the bottom ledge 58. Therefore, gas flowing down the flow tube 36 during exhalation encounters the bottom ledge 58 and is deflected around the ledge and into the outlet flow passage 60 as indicated by arrow F. From there, exhalation gas may pass through the grill 72 to ambient air as indicated by arrows G.

Upon inhalation, gas flows from ambient air through the grill 72 into the outlet flow passage 60 as shown by arrow G. From there, it flows around the bottom ledge 58 and into the bottom end of the flow tube 36 as indicated by arrow F. As shown, an additional concentric chamber 78 is defined between the outer surface 40 of the flow tube 36 and the inner surface 42 of the outer shell 34 and below the flange 46. Upon inhalation, this concentric chamber 78 acts to create turbulence in the flow, and to introduce gases to the flow tube from all radial positions as evenly as possible. The inhalation gases then flow through the flow tube 36 as shown by arrow E and make a 180° turn as shown by arrows C and D into the concentric chamber 48. From here they flow into the inlet conduit 30 as shown by arrow B and into the respiratory connector as shown by arrow A.

The above described physical configuration of the calorimeter 10 takes into consideration multiple, often contradictory, factors. It is preferred that inhalations and exhalations are not restricted as they flow through the calorimeter. Experimentation has shown that if inhalation and exhalation flow encounter any significant resistance, breathing becomes more difficult and the metabolic rate increases. It is preferred that the calorimeter measure actual metabolic rate, not a rate artificially elevated by flow resistance. Flow resistance also leads to a pressure drop through the calorimeter. It is preferred that the pressure drop through the calorimeter measure less than 3 cm of water at a flow rate of one liter per second (1 L/s). As a contradictory factor, the accuracy with which flow rates through the flow tube 36 may be measured using an ultrasonic flow measurement system increases as flow velocity increases. However, flow resistance increases with flow velocity. Therefore, there is a tradeoff between flow velocity measurement accuracy and flow resistance. Also, a longer flow path allows better measurement accuracy. However, increasing the flow path length increases the size of the calorimeter and may increase flow resistance. The above described configuration provides an excellent combination of low flow resistance, accurate flow measurement, saliva removal, and compact packaging.

Electronic Components

Referring now to FIGS. 3 and 4, a circuit board 88 is vertically mounted to the inside of the front cap 74 of the reusable main portion 24 of the calorimeter 10. This circuit board supports or interconnects with each of the electronic components of the calorimeter. An oxygen sensor 84 is mounted to the circuit board near its lower edge and extends forwardly so that it is positioned immediately behind the rear wall 62 of the recess 26. An opening 86 in the rear wall 62 allows gases in the flow passage 60 to contact the oxygen sensor 84. A gasket 87 is positioned between the oxygen sensor 84 and the back of the wall 62, around the opening 86, to prevent leakage of respiration gases past the oxygen sensor. A temperature sensor 90, an ambient pressure sensor 92, and a relative humidity sensor 94 are all mounted to the circuit board 88 in the positions shown. Obviously, these various sensors may be located in other positions if desired. As will be clear to one of skill in the art, various types of sensors may be used to measure temperature, pressure, and humidity. In one embodiment of the present invention, the temperature sensor is a thermistor, such as part number RL1005-5744-103-SA from Keystone Thermometrics, the pressure sensor is a Motorola sensor, part number MPX4115A, and the relative humidity sensor is a Honeywell sensor, part number HIH3605A. A central processing unit 96 and a speaker for the calorimeter are also mounted to the circuit board, along with an application specific integrated circuit (ASIC) 98 that forms part of the ultrasonic flow sensing system. The display screen 18 and its associated circuitry is mounted to the front side of the circuit board, behind lens 19 and aligned with the hole 76 in the front cap 74, to allow viewing of the display screen 18.

An upper ultrasonic transducer 80 is disposed in the upper wall of the recess 26 in the reusable main portion 24 of the calorimeter 10. It is connected to the circuit board 88 by wires, not shown. A lower ultrasonic transducer 82 is disposed in the bottom ledge 58 and is also connected to the circuit board 88 by wires, not shown. The ultrasonic transducers 80 and 82 form part of the ultrasonic flow sensing system and will be described in more detail hereinbelow.

In the embodiment depicted in FIGS. 3 and 4, a power supply connector 102 is provided on the circuit board 88 which aligns with a hole 104 in the side of the reusable portion 24 of the calorimeter 10. In this embodiment, a power cord, not shown, is connected to the power connector 102 and extends to a plug-in power supply for powering the calorimeter. Alternatively, the calorimeter may include internal rechargeable or replaceable batteries in place of, or in addition to, the power connector. A communication connector 106 is also mounted to the circuit board 88 and allows interconnection of the calorimeter 88 with an external device such as a computer. This communications connector may take several forms. Alternatively, or in addition, the calorimeter may include one or more wireless communication devices, such as an infrared (IR) transmitter and receiver, radio frequency transceiver (Bluetooth or other), or cellular telephone or modem device. The inclusion of a wireless communication device allows the calorimeter to transmit and/or receive data to/from local/remote computing devices, including via the Internet. A cordless phone may also be incorporated in the communication, physiological monitoring, and data processing. This and other approaches are disclosed in Mault's provisional patent application Ser. No. 60/165,166, filed Nov. 12, 1999, and which is incorporated herein by reference. As a further alternative, the calorimeter may include a slot for receiving removable memory cards. Data measured or calculated by the calorimeter may be stored on or retrieved from the removable memory card. The card may later be removed and inserted into another computing device for transfer and/or further processing of the data.

Approaches to Indirect Calorimetry

As will be clear to those of skill in the art, the above-described calorimeter provides significant packaging, air flow, and moisture removal advantages over the prior art. As will also be clear to those of skill in the art, the actual measurements and calculations necessary to determine various respiratory and metabolic parameters may be performed in a number of ways. A calorimeter constructed according to the above description and accompanying Figures may be configured for use with several of these approaches, as will be discussed in more detail hereinbelow. Therefore, it should be understood that the following description of preferred measurement and calculation approaches are not exhaustive of the approaches possible with the physical configuration of the calorimeter thus far described.

According to a first preferred embodiment of the present invention, ambient temperature, relative humidity and pressure are measured as well as inhalation volume and exhalation volume and oxygen concentration. The remaining factors are either calculated or assumed as necessary. As will be clear to those of skill in the art, each of these factors may be measured in a variety of ways.

Flow Sensing

According to the first preferred embodiment of the present invention, inhalation and exhalation volume are measured by instantaneously measuring the flow velocity of gas through the flow tube 36. Because all inhalation and exhalation passes through this tube, and the internal diameter of the tube is known, measuring flow velocity in the tube allows calculation of flow volume. According to the present invention, flow velocity in the flow tube 36 is measured using two spaced apart ultrasonic transducers.

Referring again to FIG. 4, the upper ultrasonic transducer 80 is supported in the upper wall 56 of the recess 26. The lower ultrasonic transducer 82 is supported in the bottom ledge 58 at the bottom of the recess 26. As shown, these transducers are positioned such that ultrasonic pulses traveling between the transducers 80 and 82 travel parallel to the flow in the flow tube 36 as shown by arrow E. As will be clear to those of skill in the art, transmitting ultrasonic pulses in a direction parallel to fluid flow provides advantages in measurement accuracy.

Measurement of flow velocity using ultrasonic pulses is described in U.S. Pat. Nos. 5,419,326; 5,503,151; 5,645,071; and 5,647,370, all to Harnoncourt et al., which are incorporated herein by reference. In the Harnoncourt patents, ultrasonic transducers are positioned so as to transmit pulses through a flowing fluid in a direction that has a component in the flow direction. Specifically, with fluid flowing through a tube, the transducers are positioned in the side walls of the tube at an angle such that ultrasonic pulses are transmitted at an angle to the fluid flow. Flow speed may be calculated based on the fact that ultrasonic pulses traveling with the flow travel faster while ultrasonic pulses traveling against the flow travel slower. Mathematical corrections are made for the fact that the ultrasonic pulses are traveling at an angle to the flow. Preferably, pulses are alternately transmitted in a direction with the flow and in a direction against the flow so that a time difference may be calculated.

The present invention may use ultrasonic transducers comprising a metalized polymer film and a perforated metal sheet. In one preferred embodiment, the ultrasonic flow measurement system is supplied by NDD of Zurich, Switzerland and Chelmsford, Mass. The present embodiment combines the use of ultrasonic transducers with a coaxial flow path in a novel and improved configuration.

Ultrasonic pulses are transmitted with and against the direction of flow, resulting in measurement of upstream and downstream transit times. If the gas flow rate is zero, the transit times in either direction through the gas are the same, being related to the speed of sound and distance traveled. However, with gas flow present, the upstream transit times differ from the downstream transit times. For constant flow, the difference between sequential upstream and downstream transit times is directly related to the gas flow speed.

FIG. 10 is a simplified illustration of the general configuration used in the present embodiment. Flow rates are measured using the pair of ultrasonic transducers, 80 and 82, mounted at opposite ends of a flow path, formed largely by flow tube 36. To send an ultrasonic pulse, a high voltage (approximately 200 V) is applied to one transducer, say 80, and the voltage is then quickly removed. This causes transducer 80 to resonate at its natural frequency and to function as an acoustic transmitter. A voltage of approximately 100 V is applied to the other transducer 82, enabling it to act as an acoustic receiver (or acoustic detector). The DC bias must be applied to the receiving transducer 82 in order for it to generate the maximum electrical signal. The transit time is the time between the transmission of the pulse from transducer 80 and detection of the pulse by transducer 82. The roles of transmitter and detector are then reversed, in order to measure a transit time for a pulse traveling in the opposite direction.

A series of transit time measurements of the form U1-D1-U2-D2-U3-D3 are hence obtained, where U and D refer to transit times for pulses traveling up or down the flow tube, respectively, and the numbers refer to the sequence of measurement. (The terms up and down are appropriate for the configuration shown in FIG. 10; however in other embodiments the flow orientation may be horizontal, oblique, etc.) By averaging U1 and U2, we obtain an estimated up-time at the time D1 was measured by linear interpolation. To obtain a transit time difference, and hence flow rate, at the time that D1 was measured, we compare D1 with the average of U1 and U2. Similarly, to obtain a flow rate at the time U2 was measured, we compare U2 with the average of D1 and D2. This is but one simple method of processing the measured data. Other approaches will be clear to those of skill in the art.

A schematic of the electronic drive scheme is shown in FIG. 11. Ultrasonic transducers 80 and 82 are preferably controlled by an ASIC (application-specific integrated circuit) 98, using transducer control circuitry 110. The ASIC 98 is used to control the transmission and detection of ultrasonic pulses, and communicates with the CPU (central processing unit) 96 of the calorimeter using a serial UART (universal asynchronous receiver transmitter) operating at 19.2 Kbaud. A conventional boost converter 112, regulated by the ASIC 98, is used to generate a high voltage in the range 190–230 V (DC) from the low voltage (5 V) supply 114. The high voltages are required to operate the ultrasonic transducers. The low voltage supply 114 also powers other device elements. Other electronic control schemes with similar functionality may be used.

A command is sent from the CPU 96 to the ASIC 98 to start the flow measurements. The ASIC, through control circuitry 110, applies 200 V to one transducer (say 80). This voltage is then discharged, causing an approximately 35 kHz (resonant frequency of the transducer) pulse to be emitted. At the same time, 100 V is applied to the other transducer 82. A 10 MHz clock within the ASIC 98, controlled by a crystal 116 associated with the ASIC, drives a 100 MHz counter that counts in 10 ns increments starting from the time the pulse is sent. When a 35 kHz signal is received from the detecting transducer 82, the count is stopped, and the transit time value (in the form of a number 'N' of 10 ns time intervals) is sent to the CPU 96 using the serial connection. Every 5 ms, the acoustic transmitter and acoustic receiver switch roles, so that an ultrasonic pulse is then transmitted in the opposite direction along the flow path.

A typical transit time in the present embodiment is 220 $\mu$s, or 2200×10 ns time intervals, in which case the number 2200 would be sent to the CPU as a data byte. Transit time data are sent from the ASIC to the CPU over the UART. An interrupt service routine is used to capture the serial bytes as they are received by the CPU.

Transit times for pulses traveling up and down the flow tube (up-times and down-times) and the difference between sequential measurements are stored in three separate buffers. The difference buffer is used to zero the device, so that the flow reading is zero for no actual flow. The difference buffer is also used to detect inhale, exhale, and no-flow states. There are additional instrumental delay times in the transit time measurement process, typically approximately 20 $\mu$s. These may differ for up-time and down-time measurements, and can be compensated for by subtracting the delay from the transit time data.

A software process is used to calculate the flow values, using the method of averaging e.g. two up-times and comparing with the intervening down-time (as discussed in more detail earlier). The flow values are combined with the cross-sectional area of the tube (113 mm$^2$ in the presently preferred embodiment), path length (distance between the transducers, 76 mm in the presently preferred embodiment), and calibration factors for up-flow and down-flow to obtain flow rates as well as linearization constants. The flow rates are summed over exhalation or inhalation periods to obtain flow volumes.

In the present preferred embodiment, the interrupt service routine of the CPU is used to form cumulative sums of up-times and down-times for storage in separate buffers. The software process samples these periodically, e.g. every 100 ms (20 samples). This effectively averages the flow rate measurements, leading to higher resolution in the calculated flow volumes. In the present preferred embodiment, the resolution in measured flow volume is approximately 0.9 ml/s per individual measurement, or approximately 0.045 ml/s for an average of 20 readings.

Other embodiments are possible. For example, ultrasonic flow sensors may be obtained from other sources. Some sensors use the sing-around method of flow rate determination. Ultrasonic pulses are transmitted along the flow path from one transducer to the other, a new pulse being sent once the previous pulse has been received. The frequency of pulse sending is related to the transit time along the tube. The role of transmitter and detector are reversed after some time, or some number of pulses, and a train of pulses is sent along the flow path in the opposite direction, a new pulse being sent once the previous pulse is detected. A new frequency of pulse sending is measured. Hence the equivalent of up and down times are determined from the frequency measurements, and can be treated as described above.

Micromachined ultrasonic transducer arrays are available from Sensant of San Jose, Calif. These sensors have the advantage of low noise, high frequency range, potentially lower drive voltages, and have advantages for use in the present invention. For example, pulse repetition rates may be higher, allowing instantaneous flow rates to be measured more frequently (i.e. with higher resolution), giving more accurate integrated flow volumes. Micromachined temperature, pressure, and humidity sensors may be integrated into the ultrasonic arrays, allowing the effects of these environmental factors on ultrasonic transducer performance to be compensated. For example, distortion of micromachined structures due to environmental effects may be monitored using electric capacitance. Using an array, or a number of arrays, transit time variations over the lateral dimension (perpendicular to flow direction) of the flow tube may be measured (cross-sectional flow imaging) and integrated. Different sensors on the array may be used as transmitters and detectors at the same time, allowing upstream and downstream transit times to be measured simultaneously, so that averaging methods are not required.

As will be clear to those of skill in the art, other approaches to flow sensing may also be used in place of, or in addition to, the ultrasonic flow sensing on the preferred embodiment. For example, flow rates may be determined using tiny impellers in the flow path, hot wire based mass flow meters, and pressure differential type flow meters. As will be clear to those of skill in the art, the present preferred embodiment could be adapted to use these or other approaches to flow measurement.

Oxygen Sensor

As mentioned previously, the oxygen concentration of the exhalation flow is also measured in the present invention. Specifically, instantaneous oxygen concentration is measured at the same time as flow is measured. By "instantaneous" it is meant that the oxygen sensing has a very fast response time. Preferably, the response time of an oxygen sensor for use with the present invention is 100 msec or less. In some embodiments, the response time is 30–40 msec or less.

Oxygen concentration may be measured in a variety of ways. In the presently preferred embodiment of the present invention, a fluorescence-based oxygen sensor is used to determine the partial pressure of oxygen in the exhalation.

As best shown in FIGS. 4 and 5, the oxygen sensor 84 is mounted adjacent a window 86 in the back wall 62 of the recess 26. This places the oxygen sensor 84 in contact with the inhalation and exhalation gases passing through the outlet flow passage 60. This positioning also exposes the oxygen sensor to a turbulent flow of gas, which is preferred.

Fluorescence based oxygen sensors are known in the art, for example as described by Colvin (U.S. Pat. Nos. 5,517,313; 5,894,351; 5,910,661; and 5,917,605; and PCT International Publication WO 00/13003, all of which are incorporated herein by reference). A sensor typically comprises an oxygen permeable film in which oxygen-indicating fluorescent molecules are embedded. In U.S. Pat. Nos. 5,517,313 and 5,894,351, Colvin describes sensors using a silicone polymer film, and suggests using a ruthenium complex, tris(4,7-diphenyl-1,10-phenanthroline)ruthenium (II) perchlorate, as the oxygen indicator fluorophore molecule. The orange-red fluorescence of this ruthenium complex is quenched by the local presence of oxygen. Oxygen diffuses into the oxygen permeable film from the gas flowing over the film, inducing fluorescence quenching. The time response of the quenching effect, relative to concentration changes of oxygen in the gas outside the film, is related to the thickness of the film. Thin films are preferred for a rapid response, as described in U.S. Pat. No. 5,517,313.

Referring now to FIGS. 6 and 7, the fluorescence based oxygen sensor used in the present embodiment is shown generally at 120. FIG. 6 is an exploded view and FIG. 7 is a cross sectional view. The presently preferred sensor is supplied by Sensors for Medicine and Science, Inc., based on the technology described in the Colvin patents. A circuit board 144 has a plurality of pins 149 extending downwardly for interconnecting the sensor 120, both mechanically and electrically, with the main circuit board 88 in the calorimeter. An LED 132 is mounted generally to the center of the top of the circuit board. A pair of photodiodes 134 and 136 are also mounted to the top of the circuit board 144. The photodiodes 134 and 136 are mounted symmetrically on opposite sides of, and a short distance from, the LED 132. An optical filter is mounted on top of each photodiode; filter 138 is mounted on photodiode 134 and filter 140 is mounted on photodiode 136. The optical filters are bonded to the photodiodes with an optically clear adhesive.

A heat spreader 142, preferably a thin copper sheet with downturned edges, is mounted to the top of the circuit board. The heat spreader has a downwardly extending foot 143 at each of its four corners, each of which engage a hole 145 in the circuit board 144. The feet 143 and the downturned edges of the heat spreader 142 support the central portion of the heat spreader 142 a short distance above the circuit board 144, leaving a gap therebetween. The LED 132, the photodiodes 134 and 136, and the filters 138 and 140 are disposed in this gap between the circuit board 144 and the heat spreader 142. Two round holes 146 are cut in the heat spreader, one hole being directly above each of the photodiodes 134 and 136. Two pieces of glass substrate 128 and 130 are mounted to the top of the heat spreader 142, with one piece being mounted directly on top of each of the holes 146. As shown, these pieces of substrate 128 and 130 are square. A circle of fluorescent film is formed on top of each of the pieces of substrate; film circle 122 is formed on substrate 128 and film circle 124 is formed on substrate 130. A gas impermeable glass cover 126 is disposed over film circle 124 and bonded to the glass substrate 130 with epoxy 125. Therefore, film circle 124 is sealed in by the cover 126 above and the epoxy 125 at the edges. This results in one of the film circles, 122, being exposed to the surrounding atmosphere, while the other film circle, 124, is sealed in and not exposed. Therefore, film circle 124 does not react to changes in oxygen concentration while film circle 122 does. Film circle 122 will be referred to as a sensing region and film circle 124 will be referred to as a reference region.

Referring again to FIG. 7, the gap between the circuit board 144 and the heat spreader 142, as well as the holes 146, are filled with an optically clear waveguide material 141. The waveguide material 141 serves to optically couple the LED 132 to the glass substrates 128 and 130, making the substrates an integral part of the waveguide. The waveguide material also optically couples the sensing region 122 and reference region 124 to the filters 138 and 140 and the photodiodes 134 and 136. The result is a continuous optical waveguide that optically couples these components. Suitable waveguide materials are manufactured by Norland Products of New Brunswick, N.J., and by Epoxy Technology of Bilerica, Mass., the latter under the name EPOTEK®.

In order to avoid problems with condensation forming on the sensing region 122 and the reference region 124, the regions are preferably both warmed using the heat spreader 142. For this purpose, small heaters 148, comprising resistors, are mounted to the circuit board 144 adjacent each of the foot mounting holes 145. The heat spreader feet 143 are soldered into the holes 145, and to the heaters 148 so that heat is transferred into the spreader. A thermistor 147 is mounted to the circuit board 144 in a position such that it contacts one of the downturned edges of the heat spreader 142 when the sensor is assembled. The thermistor 147 may be soldered to the edge to improve heat transfer. The thermistor 147 is then used to monitor the temperature of the heat spreader 142, and the heaters 148 are controlled so as to maintain a generally constant temperature. An EEPROM 155, containing calibration data for the oxygen sensor, is mounted to the underside of the circuit board 144.

The fluorescent films 122 and 124 are formed by an oxygen permeable film containing oxygen-indicating fluorescent molecules, such as ruthenium complexes. In the presently preferred embodiment, the oxygen permeable films are a porous glass, such as sol-gel.

Radiation from the LED 132, preferably a blue light-emitting diode (LED), is transmitted to the sensing region 122 and the reference region 124 by the optical waveguide material 141. The wavelength emission of the LED 132 is chosen to induce fluorescence from the fluorescent film regions 122 and 124; other wavelengths may be used with other fluorophores. Orange-red fluorescence emissions from sensing and reference regions are detected by the two photodiodes. Photodiode 134 detects fluorescence from the reference region 124, and photodiode 136 detects fluorescence from the sensing region 122. The photodiode outputs are fed into high-speed transconductance amplifiers, as described below. The optical filters 138 and 140 overlie the photodiodes, to pass the orange-red fluorescence radiation while rejecting other wavelengths, in particular blue radiation from the LED. The optical filters 138 and 140 may be made an epoxy coating, a glass filter, or a polymeric-based sheet material. Preferably, a prefabricated polymeric-based sheet material is used. The emissions from the LED 132 and the fluorescence emissions from the films 122 and 124 pass through holes 146 in the plate 142. Preferably, the film circles 122 and 124, the holes 146, and the active areas of the photodiodes 134 and 136 are all circles of similar diameter.

During oxygen sensing measurements, the substrates 128 and 130 and sensing region 122 and reference region 124 are maintained at approximately 45° C. to reduce problems associated with moisture condensation. The heating of the substrate is achieved by passing electrical current through the four surface-mounted resistors 148. The temperature of the copper plate 142 is monitored by the thermistor 147, allowing the heating current through the resistors and temperature to be regulated. If moisture was eliminated from the gas flow by some means, e.g. chemical drying, water absorbing/adsorbing substances, membranes, filters, foam sheets, etc., or prevented from condensing on the fluorescent film, such as by some surface treatment (an oxygen-permeable hydrophobic film or other approaches), then the oxygen sensor need not be heated. Temperature stability is improved by heating, however the oxygen sensitivity is better at lower temperatures.

Figure 12:
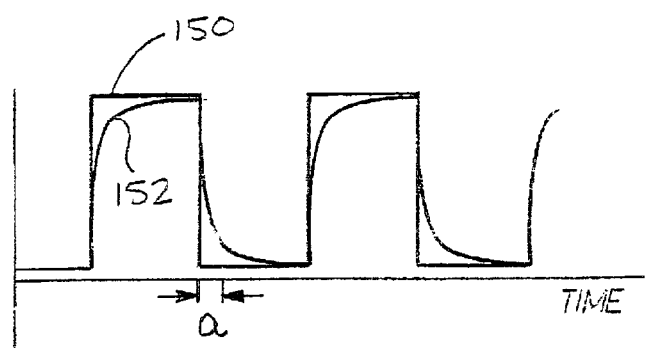
FIG. 12 is a schematic showing a drive signal and fluorescence response signal for a fluorescence based oxygen sensor for use with the present invention.

The radiation output of the LED is preferably modulated using an electrically modulated drive current. A modulation frequency of 2 kHz is used in the presently preferred embodiment. Other modulation frequencies, such as 1–10 kHz, may be used. The present embodiment determines oxygen partial pressure based on fluorescent intensity measurements, in which the decrease in fluorescence intensity due to oxygen quenching is detected. The less oxygen that is present, the more fluorescence that will be detected, the more oxygen, the less fluorescence. Each time the LED 132 is illuminated, there is a fluorescence response, the intensity of which varies depending on the amount of oxygen that is present. As known to those of skill in the art, the fluorescence response is not instantaneous, but rather there is a lag before the fluorescent material fluoresces in response to illumination by the LED 132. Likewise, there is a lag between the time the LED 32 is turned off and the time that fluorescence stops. This is known as decay time. Preferably, the time period of the applied modulation is chosen to be significantly greater than the fluorescence decay time. FIG. 12 shows schematically an example of a possible applied radiation intensity vs. time signal (the squarewave signal 150), along with a possible fluorescent response signal (the rounded signal 152). In the current embodiment, the time period of the squarewave is of the order of 0.50 msec, whereas the fluorescence decay time is on the order of 3 $\mu$sec (0.003 msec). An alternative approach to determining oxygen concentration is based on detecting changes in the fluorescence decay time, using e.g. measurements of the phase delay of a fluorescence signal relative to the excitation signal. For example, in FIG. 12, the phase delay of the fluorescence decay may be measured so as to correspond to the period shown as "a". This phase delay varies with oxygen concentration and may therefore be used as an indicator of oxygen concentration. In such fluorescence decay measurements, higher modulation frequencies may be used. The intensity modulation of the LED output may also be sinusoidal. The thickness and porosity of the fluorescent films may also be adjusted to control the diffusion-limited response time of the fluorescence signals.

Signals from the photodiode 136 (the sensing region signal) and photodiode 134 (the reference region signal) are passed through similar amplifying, filtering, and demodulation stages to obtain DC signals corresponding to the fluorescence intensity from both regions. If the reference signal and the sensing signal are of different levels at zero oxygen concentration, their respective gains in the amplifier stage may be adjusted to compensate. After amplification and conversion to DC, the sensing region signal and the reference region signal are compared to obtain a signal that is theoretically independent of error sources such as temperature change, LED intensity changes, etc. In the present embodiment, this comparison takes the form of:

Signal=Sensing Region–K*(Reference Region–Reference Baseline)

where K is an experimentally determined constant. Alternatively, the two signals may be ratioed.

Figure 13:
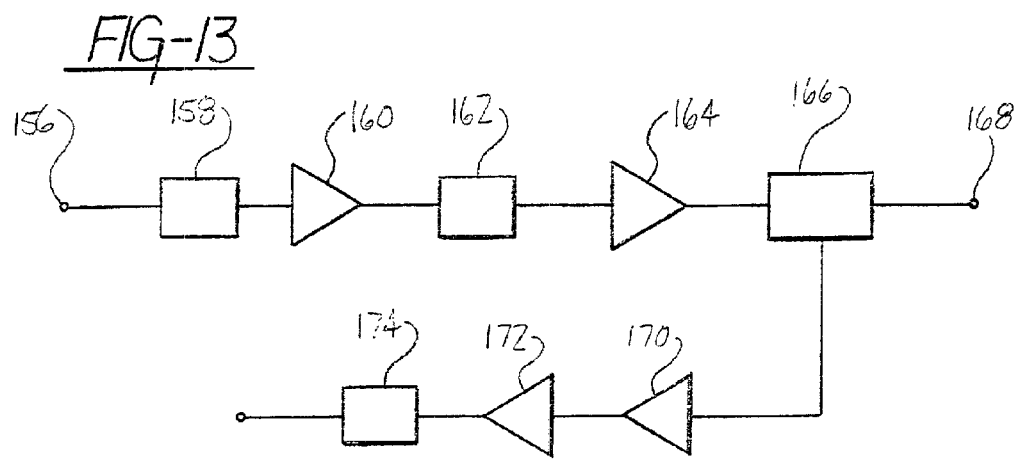
FIG. 13 is a schematic showing an electronic configuration for a fluorescence based oxygen sensing system for use with the present invention.

FIG. 13 shows a schematic diagram of the processing of the signal from photodiode 136. The signal enters at 156, is passed through a high pass filter 158 to remove DC and low frequency ambient light produced signals (e.g. low frequency stray light from electric lamps), and is passed to an inverting AC amplifying stage 160. The AC signal is passed through another high-pass filter 162 into another amplifying stage 164. The amplified AC signal is then demodulated using an analog switch 166 (based on an Analog Devices chip ADG719BRM, though other devices may be used). This switch alternates between the signal when the LED is on, and a constant reference voltage (used as the virtual ground for the amplifying stages, shown input at 168) when the LED is off. The following amplifying stage 170 alternates between a gain of 0.5 and –0.5, demodulating the signal. The signal is then passed through a further amplifying stage 172 and a low pass filter 174. The use of such a scheme, sometimes termed a synchronous amplifier, or lock-in amplifier, considerably improves the signal to noise ratio. This is a conventional technique, and other schemes may be used.

To compute the actual signal due to the oxygen sensor, a baseline measurement is first made with the LED turned off. The signal obtained with the LED turned on (and modulated) is read and subtracted from the baseline to find the final oxygen sensor signal.

Electronic Circuitry and Components

Figure 14:
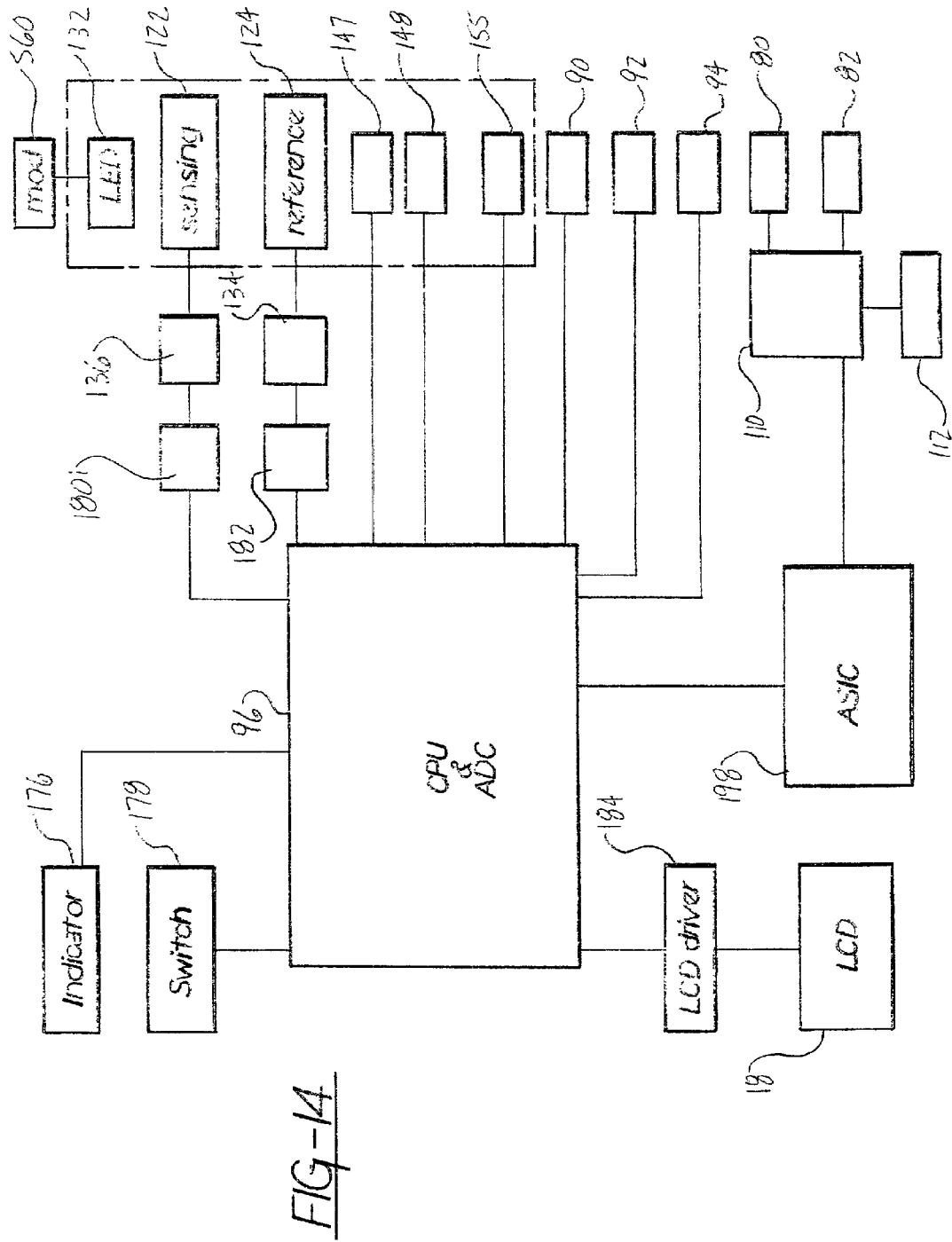
FIG. 14 is a schematic showing the electronic components of a preferred embodiment of the present invention.

FIG. 14 shows a simplified schematic of the calorimeter, in terms of its electrical configuration. The calorimeter has a central processing unit (CPU) 96 which controls the overall operation of the device.

The oxygen sensor, shown generally at 120, comprises a blue LED 132, a fluorescence quenching oxygen sensing region 122, a fluorescent reference region 124, a thermistor 147, a heater 148, and an EEPROM 155 containing calibration data for the sensor 120. The LED 132 receives a modulated drive current, controlled by oscillator/modulator 153.

The ultrasonic transducers 80 and 82 are controlled by the ASIC 98, using control circuitry 110 to direct signals and high voltage from high voltage source 112 to the sensors, and to pass detected ultrasonic pulses to the ASIC 98. The ASIC 98 and CPU 96 are connected by a serial UART.

When the device is turned on, by pressing the switch 178, the CPU directs the heater 148 to warm the fluorescent regions to approximately 45° C. An indicator light 176 shows a warming up state. The temperature of the oxygen sensor is monitored by the thermistor 147. During this period, the unit calibrates the oxygen sensor and a zero-flow test is performed, as explained later. When the sensor temperature is stabilized, as determined by the CPU from thermistor readings, the light 176 indicates that the device is ready to use.

Once the device is ready to start the breath analysis, the person breaths through the device, and the flows of inhaled air and exhaled gas are monitored by the ultrasonic transducers 80 and 82. Flow through the unit triggers data recording. Flow volumes are calculated by the CPU from serial data received from the ASIC. The ASIC determines the time between sending an ultrasonic pulse from one transducer, and receiving it using the other.

The oxygen sensor provides two electrical signals from photodiodes 134 and 136, both modulated at the same frequency as the LED 132. The signal from photodiode 134, due to fluorescence from the reference region 124, is independent of oxygen partial pressure in the gas flowing over the reference region. The signal from photodiode 136, due to the oxygen sensing region 122, is reduced in intensity (quenched) by the presence of oxygen at the sensing region. The signals from the two photodiodes are passed through similar filtering, amplification, and demodulation stages 180 and 182, to provide two respective DC voltage values, passed to the CPU via the analog-to-digital converter (ADC). The comparison of the two signals eliminates environmental effects (e.g. temperature, LED intensity), and is used to determine oxygen concentration by the CPU.

Using the calculated flow volumes and oxygen concentrations, the person's rate of consumption of oxygen is calculated by the CPU. From this, the person's metabolic rate, in the form of Kcal/day, is calculated and displayed on the liquid crystal display 18, using LCD control circuitry 184.

The CPU also receives voltage signals from environmental sensors, temperature sensor 90, pressure sensor 92, and temperature sensor 94. These signals are also used in the calculations, as described below.

Calculation of Metabolic Parameters

As will be clear to those of skill in the art, there are a number of ways to determine metabolic parameters such as $VO_2$ (volume of oxygen consumed) and RMR (resting metabolic rate). As mentioned previously, the presently preferred approach to determining metabolic parameters uses measurements of ambient temperature, pressure and humidity along with inhalation volume, exhalation volume, and oxygen concentration in the exhalation.

Figure 15:
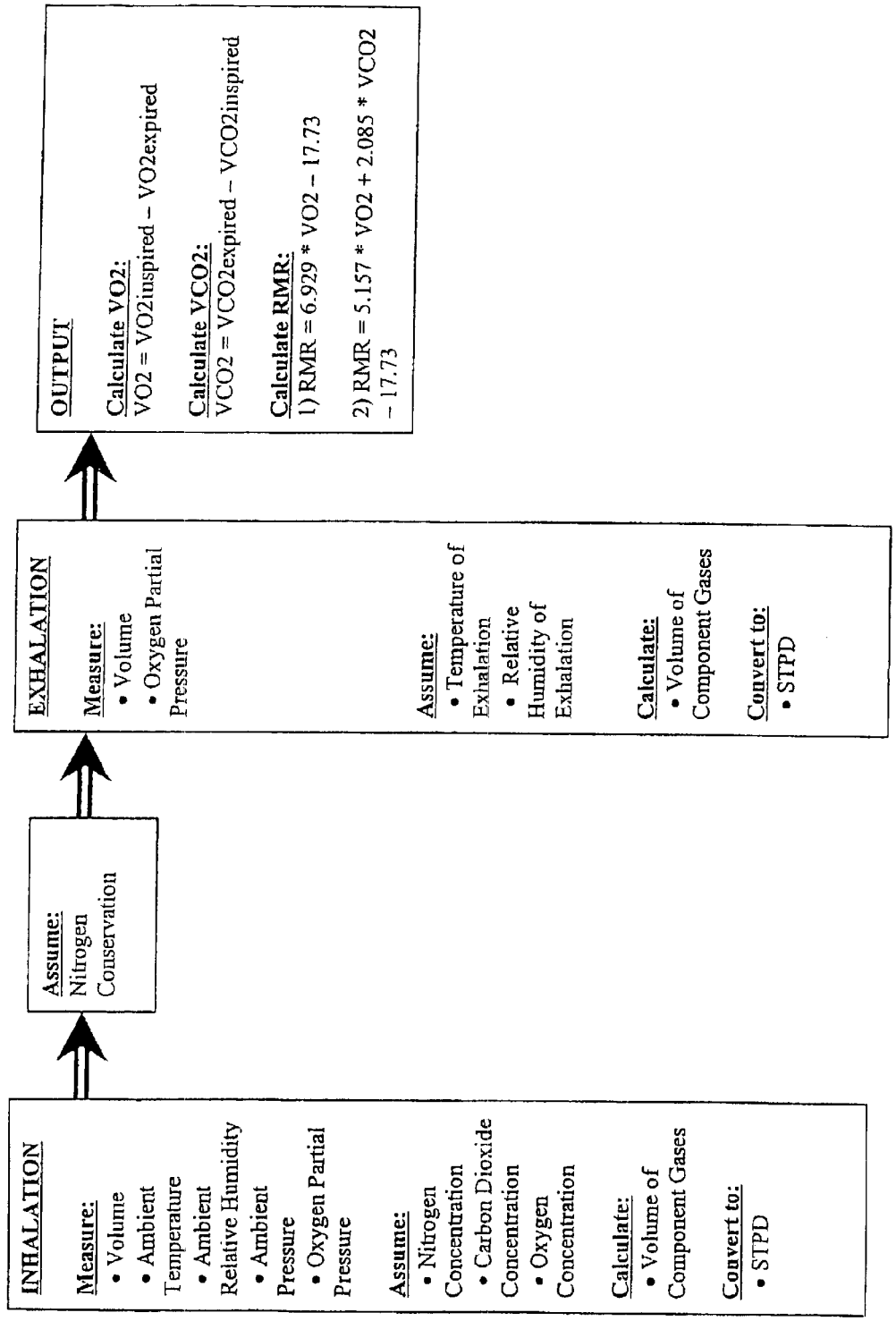
FIG. 15 is a diagram generally presenting a preferred approach to determination of respiratory parameters and calculation of metabolic rate.

Initial Considerations $VO_2$, the amount of oxygen consumed, is the difference between the amount of oxygen inhaled and the amount of oxygen exhaled. It is also desirable to determine $VCO_2$. $VCO_2$ is the volume of the carbon dioxide produced by the body and is the difference between the amount of carbon dioxide exhaled and the amount of carbon dioxide inhaled. RMR may be calculated once $VO_2$ and $VCO_2$ are known. Alternatively, certain assumptions may be made concerning the ratio between $VO_2$ and $VCO_2$, allowing RMR to be calculated from $VO_2$ alone. Therefore, a primary purpose of the present invention is to determine $VO_2$. This requires determination of both the amount of the oxygen inhaled and the amount of oxygen exhaled. It is preferred to also determine $VCO_2$ as this allows other metabolic parameters to be determined. To determine $VCO_2$ requires measurement or calculation of both the amount of carbon dioxide inhaled and the amount of carbon dioxide exhaled. The method and calculations used in the first preferred embodiment of the present invention are represented schematically in FIGS. 15 and 16.

Inhalation

The volume of oxygen inhaled, $V_1O_2$, may be calculated by multiplying the volume of air inhaled by the fraction of that air which is oxygen. The fraction of dry air that is oxygen varies only slightly from location to location and can therefore be assumed to be 20.946 percent. However, the actual air we breathe is not dry air, but instead includes a varying portion of water vapor. In order to determine the portion of the inhaled air which is oxygen, the volume of the inhalation which is attributable to water vapor must be determined and subtracted to provide a dry air measurement. As mentioned previously, a temperature sensor 90, a relative humidity sensor 94, and an ambient pressure sensor 92 are all mounted on the circuit board 88 inside the case of the reusable main portion 24 of the calorimeter 10. Theoretically, these should provide values for the temperature, pressure and humidity of the air inhaled by the user. However, under some conditions, the temperature inside the case of the reusable main portion 24 may differ from ambient temperature. This may be due to warming of the case by the user's hand, heating by the internal electronics, and heat absorbed from exhalations. Therefore, it is preferred that a correction be made to the temperature values received from the ambient temperature sensor 90. If the relative humidity sensor 94 were actually positioned in ambient air, instead of inside the case, its output would reflect the relative humidity in the ambient air. Since the relative humidity sensor 94 may be at an elevated temperature, its output indicates the relative humidity at this elevated temperature, rather than at true ambient conditions. Because the case is not hermetically sealed, it is assumed that the partial pressure of water inside the case is the same as the partial pressure of water in the surrounding atmospheric air. The partial pressure of water vapor, $ppH_2O$, can be computed from the following relationship:

$$ppH_2O = RH \times VpH_2O(t) \tag{a}$$

where RH is relative humidity in percent, and $VpH_2O$ is the vapor pressure of water, and t is temperature. $VpH_2O$ is a function of temperature and can be obtained from a look-up table or using an empirical curve fit. Therefore, the partial pressure of water vapor, ppH2O, in the atmospheric air can be calculated from the known relative humidity and temperature inside the case.

Referring to FIG. 16, a typical 750 mL total volume inhalation is shown at the far left side of the chart. This volume includes water vapor. The volume of water vapor in the inhalation may be determined according to the following equation:

$$VH_2O = \frac{ppH_2O}{Pamb} \times Vtotal \tag{b}$$

where $VH_2O$ is the volume of water vapor, $ppH_2O$ is a partial pressure of water vapor, Pamb is the ambient pressure, and Vtotal is the total volume of the inhalation. In the example shown in FIG. 16, the ambient temperature, pressure and humidity (ATP) are a temperature of 23° C., a pressure of 755 mmHg, and a relative humidity of 35 percent. Using the above equations, the total volume of water vapor may be looked up in a table or calculated to be 7.28 mL out of the 750 mL total inspired volume. The amount of water vapor in the inhalation may then be subtracted from the total, giving a dry volume of 742.72 mL.

The percentage of dry air attributable to $CO_2$, $O_2$, and nitrogen and other gases is known from a variety of sources, examples of which are given in the following chart:

| Component | % of dry air |
|---|---|
| Other (Argon) | 0.937 |
| $CO_2$ | 0.033 |
| $O_2$ | 20.946 |
| $N_2$ | 78.084 |

By multiplying these percentages by the total volume of dry air, the volume of each component gas may be calculated giving the values shown in the left-hand bar of FIG. 16. These volumes represent the volumes of each of the component gases at ambient conditions.

As shown for the example of FIG. 16, the volume of oxygen inhaled at atmospheric conditions 155.57 mL. However, this is at atmospheric conditions, which vary from location to location and time to time. Therefore, it is necessary to convert the volumes of each of the component gases to a standard temperature, pressure, and humidity, STPD (standard temperature and pressure, dry). The calculations typically used for RMR assume an STPD of 0° C., 760 mmHg and 0 percent relative humidity.

As known to those of skill in the art, conversion between one atmospheric condition and another is a simple matter of a ratio based on temperature and pressure. However, in the present case, actual atmospheric temperature is not known because the temperature sensor may be at an elevated temperature.

As known to those of skill in the art, the speed of sound is a function of ambient temperature, the water vapor mole fraction, ambient pressure, and $CO_2$ mole fraction. This relationship is disclosed in *The Journal of the Acoustical Society of America*, Vol. 93, No. 5, May 1993, pp. 2510–2516, the contents of which is incorporated herein by reference. The equation takes the form of:

$$c = a_0 + a_1 t + a_2 t^2 + (a_3 + a_4 t + a_5 t^2)x_w + \\ (a_6 + a_7 t + a_8 t^2)p + (a_9 + a_{10}t + a_{11}t^2)x_c + \\ a_{12}x_w^2 + a_{13}p^2 + a_{14}x_c^2 + a_{15}x_w p x_c, \quad (c)$$

where the coefficients are defined in the following table:

| Coefficients | Value |
| --- | --- |
| $a_0$ | 331.5024 |
| $a_1$ | 0.603055 |
| $a_2$ | −0.000528 |
| $a_3$ | 51.471935 |
| $a_4$ | 0.1495874 |
| $a_5$ | −0.000782 |
| $a_6$ | −1.82 × 10$^{-7}$ |
| $a_7$ | 3.73 × 10$^{-8}$ |
| $a_8$ | −2.93 × 10$^{-10}$ |
| $a_9$ | −85.20931 |
| $a_{10}$ | −0.228525 |
| $a_{11}$ | 5.91 × 10$^{-5}$ |
| $a_{12}$ | −2.835149 |
| $a_{13}$ | −2.15 × 10$^{-13}$ |
| $a_{14}$ | 29.179762 |
| $a_{15}$ | 0.000486 | and where c is the speed of sound, t is the ambient temperature, $x_w$ is the water vapor mole fraction, p is ambient pressure and $x_c$ is the $CO_2$ mole fraction. Several of these variables have known values. The $CO_2$ mole fraction in ambient air may be assumed since its standard value is known and varies only slightly from location to location. Ambient pressure may be determined with high accuracy by the ambient pressure sensor in the calorimeter case. Also, the speed of sound may be measured by the flow meter during inhalation.

Because the ultrasonic flow meter preferably used with the present invention transmits ultrasonic pulses in both upstream and downstream directions, the transit time, independent of flow speed, in ambient air may be determined by averaging the upstream and downstream transit times during inhalation of ambient air. The speed of sound may then be calculated according to the following equation.

$$c = L/2 \times (1/t_u + 1/t_d), \quad (d)$$

where c is the speed of sound, L is the distance between the transducers, $t_u$ is the transit time in the up direction, and $t_d$ is the time in the down direction.

This leaves essentially two variables, ambient temperature and water vapor content. Relative humidity and ambient temperature are interrelated by equation (a). Rearranging and solving for relative humidity gives:

$$RH = \frac{pp H_2 O}{V p H_2 O(t)} \quad (e)$$

At this point, the partial pressure of water, ppH2O is known based on the output of the humidity sensor 94 and the assumption that the partial pressure is the same inside and outside the case. However, equation (c) is expressed in terms of the water vapor mole fraction, $x_w$, rather than relative humidity. Therefore, three additional equations are required. The mole fraction of water vapor may be calculated as follows:

$$X_w = RH \times f \times \frac{p_{sv}}{p} \quad (f)$$

where RH is the relative humidity expressed as a fraction, f is the enhancement factor, and $p_{sv}$ is the saturation vapor pressure of water vapor in air:

$$f = 1.000\ 62 + 3.14 \times 10^{-8} p + 5.6 \times 10^{-7} t^2 \quad (g)$$

and $$p_{sv} = \exp(1.281\ 180\ 5 \times 10^{-5} t^2 - 1.950\ 987\ 4 \times 10^{-2} t + \\ 34.049\ 260\ 34 - 6.353\ 6311 \times 10^{-3} /t) Pa. \quad (h)$$

When equations (c), (e), (f), (g) and (h) are combined, this leaves two unknown variables, temperature and relative humidity. As known to one of skill in the art, the equations may be solved for the two remaining variables in a variety of ways. According to one presently preferred approach, equations may be solved through an iterative process.

First, an initial temperature estimate is made. The temperature indicated by the temperature sensor may be used as a starting point. Relative humidity is then determined according to equation (e). Then, the relative humidity just calculated is used in equation (c) to calculate temperature. The calculated temperature is plugged back into equation (e) to calculate a new relative humidity. The process is repeated until the values converge, which typically occurs after several repetitions.

At the end of this process, the actual ambient temperature of the air being inhaled is known. Together with the measured ambient pressure, ambient conditions are now known. The volumes of each of the component gases are then converted to STPD. Alternatively, or in addition to the above approach, ambient temperature or temperature in the flow tube may be directly measured using any type of suitable temperature sensor. As one example, a temperature sensor may be mounted inside the case of the calorimeter and a small fan could be used to continuously move ambient air past the sensor so that accurate readings are obtained. Other approaches will be clear to those of skill in the art.

When converted to STPD, the inhaled volume of gases have the value shown in the second bar of FIG. 16. As shown, the corrected inhaled volume of oxygen, $V_i O_2$ is 143.48 mL and the corrected inhaled volume of carbon dioxide, $V_i CO_2$ is 0.23 mL.

Oxygen Sensor Calibration

As mentioned previously, the percent of oxygen in the inhaled air may be measured or assumed. In the above explanation, the concentration or percentage of oxygen is assumed, since this value varies only slightly from location to location. However, the oxygen sensor 84 does respond to the presence of oxygen in the inhalation. Therefore, the output of the oxygen sensor during inhalation may be used to calibrate the oxygen sensor as often as during each inhalation. In theory, an ideal oxygen sensor varies its output only in response to changes in the concentration of oxygen, and does not respond to changes in other parameters such as temperature, humidity, and total pressure. However, the actual oxygen sensor is not entirely immune to changes in other parameters.

Figure 17:
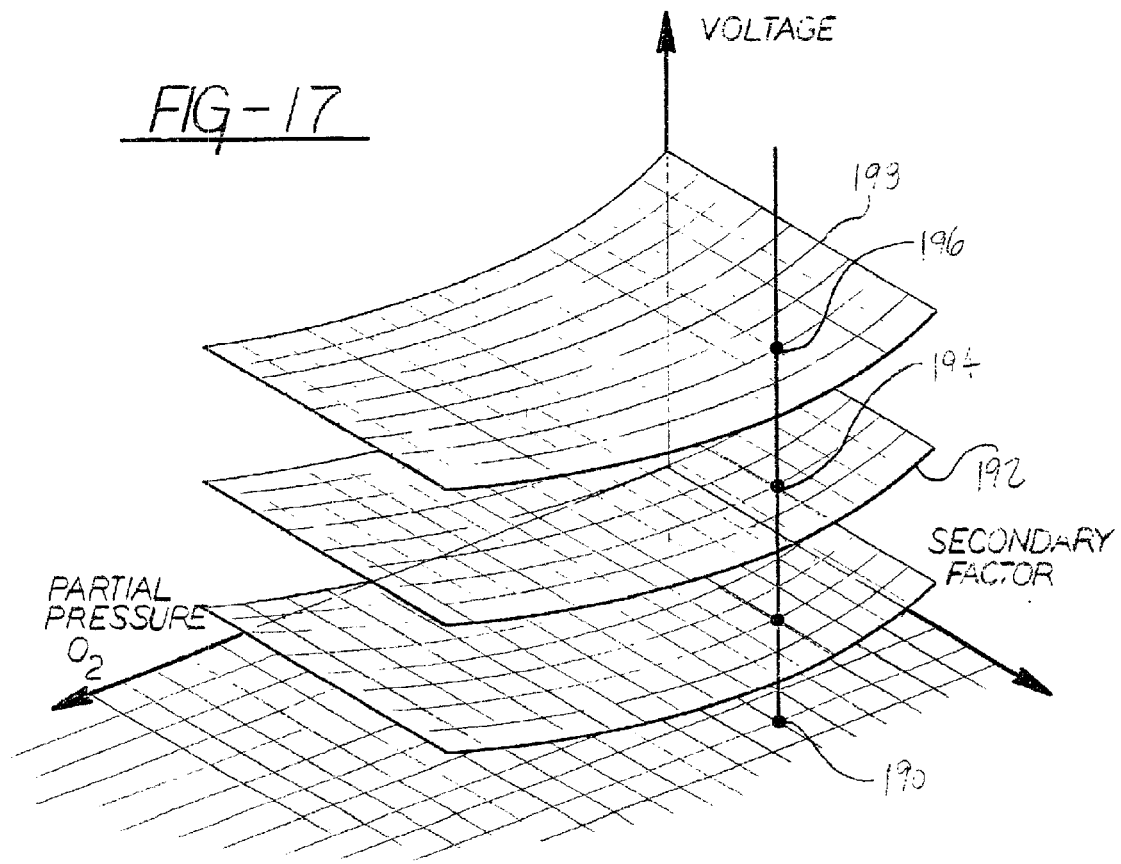
FIG. 17 is a graph showing a series of curved surfaces representing the change in voltage output of the oxygen sensor with respect to changes in the partial pressure of oxygen and an arbitrary second factor.

FIG. 17 shows a series of curved surfaces representing the change in voltage output of the oxygen sensor with respect to changes in the partial pressure of oxygen and an arbitrary second factor. This Figure is for illustration purposes only, and therefore the second factor may be thought of as representing any or all of the other parameters to which the sensor actually responds. Because the concentration of oxygen and the values for other parameters such as humidity, temperature, and pressure are known during inhalation, a point 190 may be plotted as representing the combination of the known oxygen partial pressure and the other factors. Extending upwardly from this point, it may be seen that the theoretical or tested output curve 192 for the oxygen sensor predicts an output voltage corresponding to point 194. If the actual voltage output of the oxygen sensor under these known conditions differs from this value, a correction may be applied to the output curve to correct for this difference. For example, if the oxygen sensor actually puts out a voltage corresponding to point 196, a gain factor may be applied to the primary output curve 192 so as to "move" the curve to the curve shown at 198. This allows continual fine-tuning of the output of the oxygen sensor to improve its accuracy during measurement of subsequent exhalations.

Exhalation

During exhalation, total volume and oxygen partial pressure are measured using the flow meter and oxygen sensor respectively. As is known to those of skill in the art, the temperature and humidity of an exhaled breath are reasonably constant from individual to individual. Specifically, the temperature of exhalation at the mouth averages 34.5° C. for most healthy individuals. Exhaled breath is also 100 percent saturated with water vapor, giving 100 percent relative humidity. Experimentation with the present invention has established that the temperature of exhaled breath averages approximately 32.5° C. at the midpoint of the flow tube 36. The pressure in the flow tube is substantially identical to ambient pressure due to the low amount of restriction present in the calorimeter. The conditions of the exhaled breath may be referred to as exhaled temperature pressure saturated (ETPS). In order to determine the volume of oxygen at ETPS, the following equation is used.

$$V_E O_2 = \frac{ppO_2}{Pamb} \times Vtotal$$

where $V_E O_2$ is the exhaled volume of oxygen, $ppO_2$ is the partial pressure of oxygen, Pamb is the ambient pressure, and Vtotal is the total exhalation volume. In the example shown in FIG. 16, the total exhalation volume is 800 mL, the partial pressure of oxygen is 121.6 mmHg, and the ambient pressure is 755 mmHg. This gives an exhaled volume of oxygen at ETPS of 128.05 mL. In order to make the RMR calculation, it is necessary to convert this value to STPD.

The exhaled volume of $O_2$ at ETPS may be converted to STPD by scaling for the differences in temperature and pressure. This gives an exhaled volume of $O_2$ at STPD of 114.43 mL. The volume of $O_2$ consumed by the user during the single breath is calculated by subtracting the expired volume of oxygen from the inspired volume of oxygen. Multiplying by the number of breaths during a minute gives the amount of oxygen consumed during a minute.

Preferably, the production of $CO_2$ should also be determined. In order to do this, additional calculations are required. First, certain assumptions may be made about the temperature and humidity of exhaled breath. The volume of water vapor in the exhaled breath may be determined from the assumed relative humidity and temperature, and the measured flow volume. Removing water vapor to convert to dry air leaves a total volume of 761.68 mL. Also, it is assumed that nitrogen ($N_2$) and trace gases are conserved in the lungs. Therefore, the volume of nitrogen and trace gases inhaled equals the volume of nitrogen and other gases exhaled at STPD. This assumption improves as data is summed for multiple breaths.

As shown in FIG. 16, the volume of nitrogen and trace gases may be converted from STPD to ETPS, giving a volume of 605.74 mL. At this point, the volume of water vapor, oxygen, and nitrogen and trace gases is known at ETPS. Also, the total volume is known. Therefore, the volume not accounted for by water vapor, oxygen, and nitrogen and trace gases is attributable to $CO_2$. This gives a $CO_2$ volume of 27.89 mL at ETPS. This value is then converted to STPD, giving an exhaled volume of carbon dioxide of 24.92 mL at STPD. The volume of $CO_2$ produced by the user during the single breath is calculated by subtracting the inspired volume of carbon dioxide from the expired volume of carbon dioxide. Multiplying by the number of breaths during a minute gives the amount of carbon dioxide produced during a minute.

Calculation of Resting Metabolic Rate

As known to those of skill in the art, resting metabolic rate (RMR) may be calculated in a variety of ways. One known and accepted approach is given by the de Weir formula, which takes the form:

$$RMR = 1.44(3.581 \times VO_2 + 1.448 \times VCO_2) - 17.73$$

where $VO_2$ is the volume of oxygen consumed in milliliters-per-minute, $VCO_2$ is the amount of $CO_2$ produced in milliliters-per-minute, and RMR is the resting metabolic rate in Kcal per day. As an alternative, certain assumptions may be made concerning the ratio between $VO_2$ and $VCO_2$. Specifically, the respiratory quotient is given by the following formula:

$$RQ = \frac{VCO_2}{VO_2}$$

where RQ represents respiratory quotient. The respiratory quotient typically ranges between 0.7 and 1.1 depending on the type of stored energy source being metabolized by the user's body. RQ may be assumed to be 0.85 for typical users during the calculation of resting metabolic rate. Therefore, using this ratio and substituting for $VCO_2$ gives the equation:

$$RMR = 6.929 \times VO_2 - 17.73$$

where RMR is resting metabolic rate in Kcal per day, and $VO_2$ is the volume of oxygen consumed by the user in milliliters-per-minute. Preferably, the various parameters which are measured by the calorimeter are summed or averaged over multiple breaths, thereby giving improved accuracy.

As an alternative, a $CO_2$ sensor may be incorporated into the calorimeter so as to directly measure, rather than calculate, $CO_2$ concentrations. This allows more accurate calculations of RMR as well as calculation of RQ.

Use of the Calorimeter

When the calorimeter is first turned on, the unit goes through a warm up and calibration period. During this time, the oxygen sensor heater is turned on and warms the oxygen sensor to a steady state value. During this time, the oxygen sensor is also turned on. Once the oxygen sensor has reached steady state, a zero-flow test is performed. During the zero-flow test, the flow sensor measures flow speed through the flow tube. Since the calorimeter is not being used at this stage, there should be zero flow through the flow meter. However, if the flow meter indicates a slight flow in one direction or another, an offset is assigned to re-establish zero. A variety of approaches to this zeroing may be used, though it is preferred that multiple readings are taken prior to application of an offset factor. Also, during an actual test, the flow meters may be dynamically re-zeroed during known periods of zero flow.

To use the calorimeter to calculate a subject's resting metabolic rate (RMR), it is preferred that the subject sit or relax in a comfortable position and then bring the respiratory connector into contact with their face or mouth, after the calorimeter has been turned on and allowed to warm up and self-calibrate, as previously described. The subject then breathes normally through the calorimeter for a period of several minutes. Typically, users require some amount of time before their breathing and measured metabolic rate stabilizes. Therefore, it is preferred that initial data not be used as an indication of resting metabolic rate. As will be clear to those of skill in the art, there are a variety of approaches which allow the calorimeter to most accurately determine resting metabolic rate. According to one preferred approach, once the calorimeter detects breath flow through the calorimeter, it waits 30 seconds then begins recording. However, this period of time may be increased or decreased. Once recording begins, the calorimeter makes measurements of flow, oxygen concentration, and speed of sound. Oxygen partial pressure is measured every tenth of a second, and flow velocity and speed of sound are measured 200 times per second. Flow velocity and speed of sound measurements are averaged so as to obtain a value every tenth of a second for computation of volumes. The calorimeter accumulates this data to calculate volume inspired, volume expired, inspired oxygen concentration (for calibration purposes), expired oxygen concentration, ambient temperature, ambient humidity, and ambient pressure. Ten breaths are then averaged in order to obtain one breath block. At the end of each breath block, $VO_2$ is calculated for the block. In order to determine steady state, three blocks are checked to see whether they are within a certain percentage of each other. For example, if the previous two blocks are both within 7 percent of the current block, the block is flagged as steady state. It is determined that steady state has been reached when a certain number of consecutive blocks are flagged as steady state, such as four or five breath blocks, and then $VO_2$ and $VCO_2$ are used to calculate RMR, which is displayed on the display 18. Typically, people take 8 to 10 breaths per minute so a breath block is about one minute long. Obviously, the data may be processed in other ways. Also, certain error states may be indicated. For example, if breathing is occurring too rapidly or too slowly, an error signal may be indicated. Also, errors may be indicated for too high of a flow rate, an RMR that is out of an acceptable range, for hardware errors, or for other reasons.

As mentioned previously, it takes most users some time to stabilize their breathing and indicated rested metabolic rate. However, according to another aspect of the present invention, data during the "settling down period" may be used to predict the data during the steady state period.

A person should be fully relaxed for the measured metabolic rate to be the rest metabolic rate. However, the person's breathing will often be affected by the presence of the mouthpiece or mask, particularly during the time immediately following placing the mask over the person's nose and mouth. Accurate measurements may be delayed a certain time period, e.g. 2 minutes, after the mouthpiece has been put in place, after which the person's breathing may return to normal. However, the person may not feel comfortable with the mouthpiece in place for so long.

Figure 18:
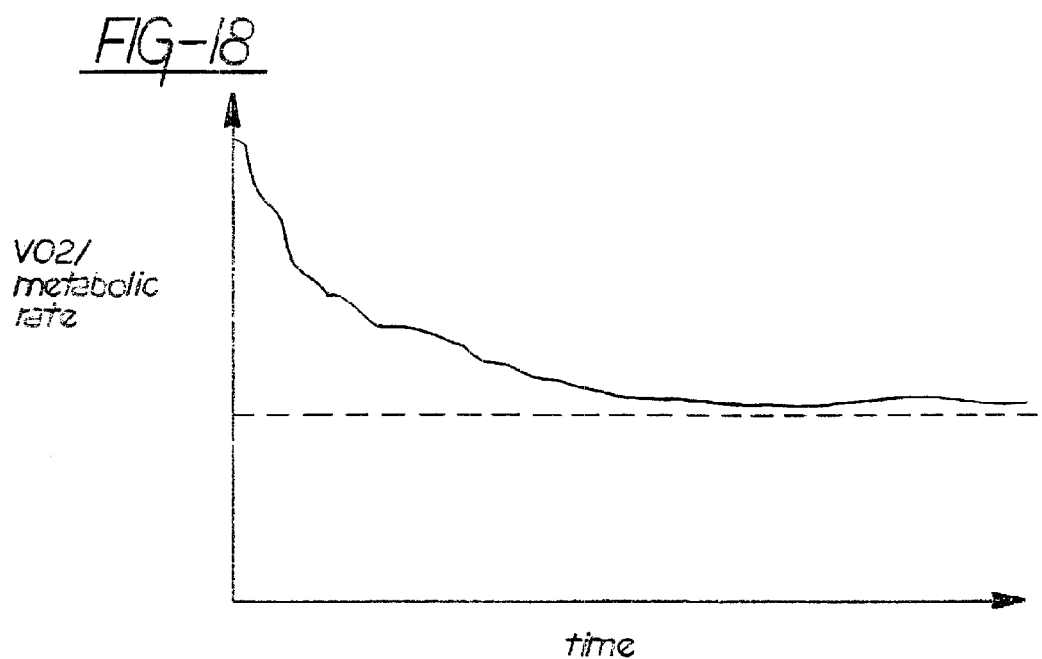
FIG. 18 is a graph showing an example of how calculated metabolic rate for a subject may change during a test.

In order to reduce the time necessary to determine an accurate value of metabolic rate of a person, algorithms may be used to extract a resting level of $VO_2$ from data that is tending towards the resting value. FIG. 18 illustrates a possible data set of $VO_2$ measurements (and hence measured metabolic rate) vs. time for a person obtained using an indirect calorimeter. Oxygen consumption is measured as a function of time, e.g. breath by breath, or by blocks of a certain number of breaths, e.g. 10. In FIG. 18, the measured oxygen consumption, shown by a solid line, approaches a value corresponding to the true resting metabolic rate, shown by a dashed line, as time advances. The person's actual metabolic rate may be constant during the measurements, with $VO_2$ measurements initially high due to breathing anomalies, but in other cases the metabolic rate itself may fall slowly towards a true value of rest metabolic rate. Both cases can be modeled. The obtained data is fit to a mathematical equation, (e.g. in terms of polynomials, exponentials, logarithmic functions, other functions, etc.) in terms of a number of parameters, including the resting metabolic rate. The resting metabolic rate is determined from a fit to the data, and the error in this measurement is estimated from the quality of the fit to the data. This process can be executed continuously in real time, as the respiratory analysis proceeds, so that the measurements can be stopped, and the mouthpiece removed, once an accurate measurement has been made. Alternatively, the data can be saved and the numerical analysis made after the test is complete.

The exact form of the data fit used will depend on the person's response to the mouthpiece and other testing conditions. In this example, for the case illustrated in FIG. 18, data might be fitted to an expression of the form $$VO_2 = A + B \exp(-t/C)$$

where A is the value of $VO_2$ corresponding to the true resting metabolic rate, B is a measure of breathing abnormality at the onset of testing, and C is a measure of how quickly breathing returns to normal after the beginning of the test. After a number of initial tests on a person, a suitable equation can be chosen to model that person's breathing response to testing. Alternatively, a model may be chosen based on the age or other demographic data relating to the person. The first breath, or first few breaths, may be discarded from the data to improve the fitting.

Subsequent respiratory analysis may then be shortened by this analysis, e.g. using a method described below, or other method.

(a) After initial testing, the time taken for breathing to fall to close to normal can be determined, and hence used to determine the length of the testing. Data can be excluded from the first part of the test, and averaged over the remaining measurements. For example, if the above equation is applicable, data obtained before some multiple (integer or fractional) of C has passed may be discarded (e.g. if C=10 seconds, data taken during the first 30 seconds of the test may be discarded, and the remaining data averaged).

(b) If the data from the test is being analyzed in real time, the test can be ended once an acceptable fit to the data has been obtained.

(c) Data may be viewed by a professional as the test is in progress, and the test stopped once the professional judges data of sufficient quality has been determined. This judgment will be based on experience.

For a person breathing through the calorimeter of the present invention, the data can be stored by the calorimeter time, and then transmitted to another electronic device for display, analysis, etc. Data may also be transmitted to another electronic device while the test is in progress (i.e. in 'real time'). Data transfer from the calorimeter to another device may use flash cards (memory cards), wireless transmission (e.g. Bluetooth), cables, IR transmission, or other electromagnetic or electrical methods, or by plugging the calorimeter into the other device. The use of flash cards is disclosed more fully in Mault's provisional patent application Ser. No. 60/177,009 filed Jan. 19, 2000, and incorporated herein by reference. The calorimeter may further comprise computing means for performing data analysis.

Under certain circumstances, a user may never reach steady state during a test. Under these circumstances, the calorimeter may indicate that no reading was possible, or a steady state value may be estimated. According to one approach, the breath blocks during the test may be averaged with some additional weighting given to blocks towards the end of the test when it is assumed that the user is closer to steady state. Obviously, detailed data recorded by the calorimeter may be observed by an experienced professional to determine the reliability of the data. For example, the calorimeter may be interconnected with a desktop computer which records and/or displays data on a measurement-by-measurement or breath-by-breath basis. In this way, the professional may observe that the subject is having trouble reaching steady state and may provide counseling or suggestions on how to better interact with the device. Also, the detailed data may provide other valuable indications about the subject.

Calorimeter Embodiments with Improved Hygiene

It is preferred that a calorimeter according to the present invention be able to safely be used by multiple users without undue risk of transferring pathogens from one user to another. In the previously discussed preferred embodiment of the present invention, each individual user is given their own disposable portion along with its respiratory connector. A fitness facility or a doctor may then own the reusable portion. As an alternative, each individual user may own a complete calorimeter and the disposable may merely be removable for cleaning purposes. However, it is preferred that the calorimeter be designed such that pathogens are not easily transferred from one user to another. Several improved sanitation versions of the present invention are disclosed in FIGS. 19–26 and an alternative oxygen sensor configuration is shown in FIG. 9.

Figure 19:
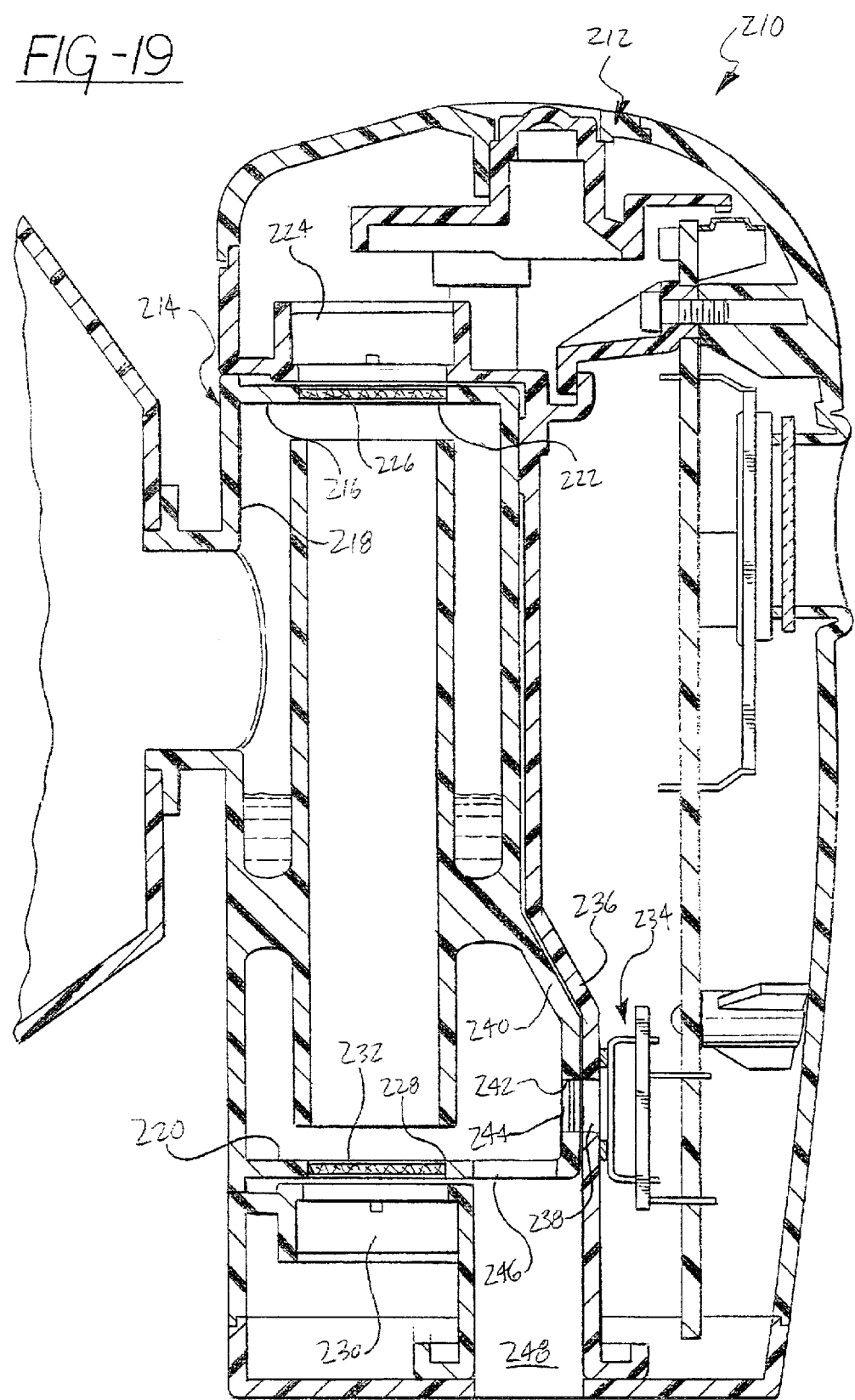
FIG. 19 is a cross sectional view of a second embodiment of the present invention that is configured for improved sanitation.

Referring first to FIG. 19, a calorimeter according to the present invention is generally shown at 210. This calorimeter has a reusable main portion 212 that is similar to the reusable main portion 24 discussed earlier. However, in the embodiment shown in FIGS. 3 and 4, the user's inhalation and exhalations may come in contact with the ultrasonic transducers 80 and 82, the oxygen sensor 84, and the surfaces in the outlet flow passage 60. These form part of the reusable portion and therefore are not disposed or changed from user to user. The embodiment of FIG. 19 is altered so as to prevent contact of the user's breath with the transducers and oxygen sensor. The disposable portion 214 has a ceiling 216 closing off the upper end of outer shell 218 and a floor 220 closing off the lower end of the outer shell 218. A hole 222 in the ceiling 216 aligns with the upper ultrasonic transducer 224 and has a piece of germ barrier material 226 disposed in the hole 222. The barrier material may be any of a variety of materials that block the passage of pathogens but allows a passage of ultrasonic pulses. Likewise, a hole 228 is defined in the floor 220 that aligns with the lower ultrasonic transducer 230. A piece of germ barrier material 232 is also disposed in this hole 228. The oxygen sensor 234 in this embodiment is moved upwardly somewhat compared to the earlier disclosed embodiment. An opening 238 is formed in the back wall 236 of the recess in the main portion 212 with the opening 238 aligning with the oxygen sensor's forward sensing surface. The outer shell 218 of the disposable 214 has a rearward wall 240 extends down past this opening 238 and joins with the floor 220 of the disposable portion 214. An opening 242 is defined in this rearward wall 240 and a membrane 244 is disposed across the opening. The membrane is of the type that allows free passage of oxygen to the oxygen sensor, but does not allow passage of pathogens. A passage 246 is cut in the floor 220 of the disposable portion 214 allowing flow to pass into an outlet passage 248 defined in the reusable portion. This passageway 248 is large and has smooth sides to allow easy flow of inhalations and exhalations. The side walls of this passage 248 may be coated with an anti-bacterial and/or anti-viral substance to prevent contamination. Alternatively, the passageway may be cleaned between uses. As a further alternative, a disposable sleeve may be inserted into this passageway, which mates with the opening in the floor of the disposable portion. The sleeve would also be removed and disposed between users.

Figure 20:
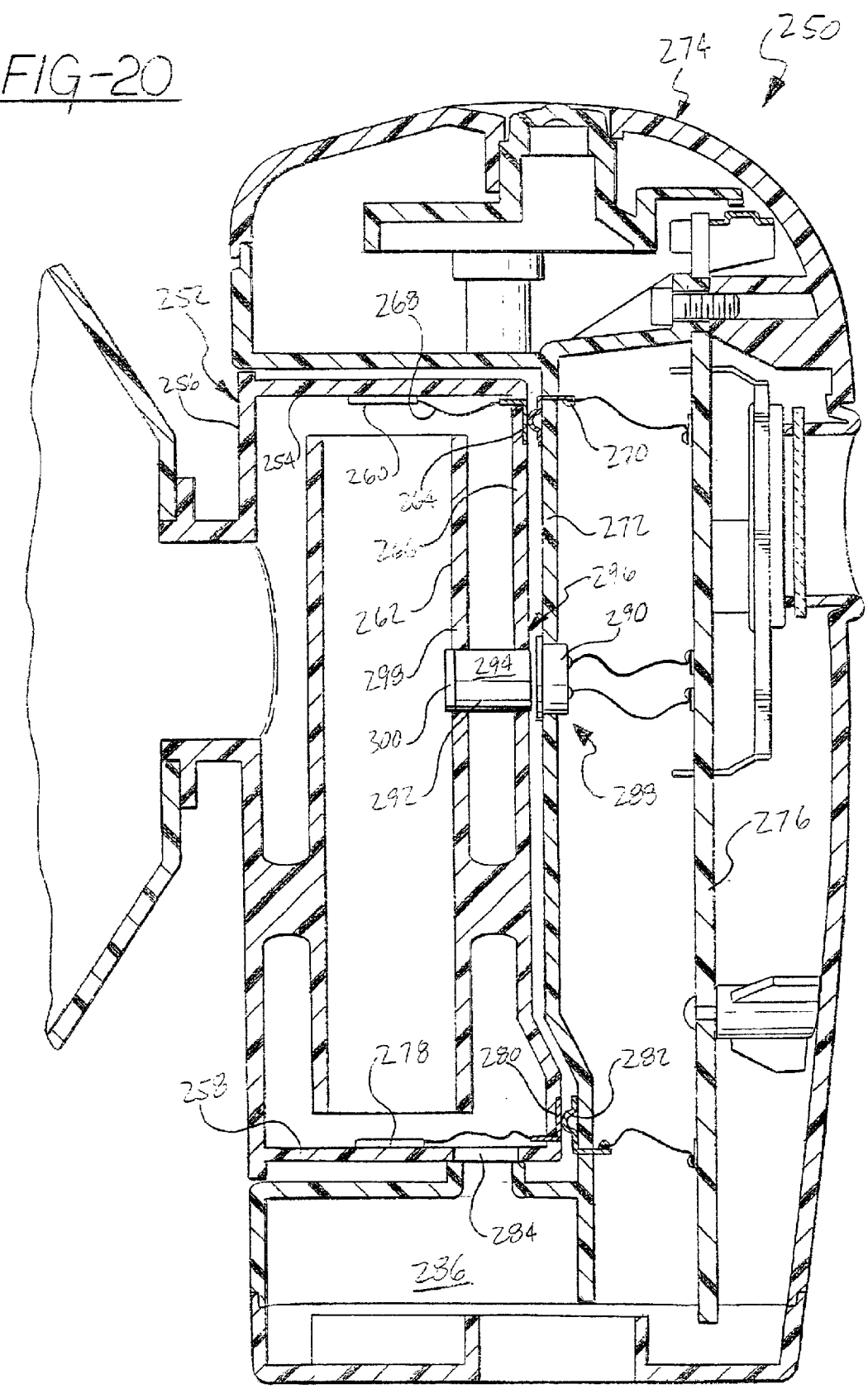
FIG. 20 is a cross sectional view of a third embodiment of the present invention with an alternative configuration for improved sanitation.

Referring now to FIG. 20, another alternative improved sanitation version of a calorimeter according to the present invention is generally shown at 250. As with the previously described version, the disposable portion 252 of the calorimeter 250 includes a ceiling 254 closing off the upper end of the outer shell 256 and a floor 258 closing off most of the lower end. In this version, a thin micromachined ultrasonic transducer 260 is mounted to the lower side of the ceiling 254 of the disposable portion 252 directly above the upper end of the flow tube 262, which forms part of the disposable portion. This thin ultrasonic transducer 260 replaces the larger ultrasonic transducers discussed in the earlier embodiments. The transducer may be a micromachined ultrasonic transducer array such as the ones produced by Sensant of San Jose, Calif.

Electrical contacts 264 are disposed in the rear wall 266 of the disposable portion 252, directly behind the transducer 260 and are electrically connected, such as by wires 268, to the transducer 260. Corresponding electrical contacts 270 are disposed on the rear wall 272 of the recess in the reusable portion 274 of the calorimeter 250 and align with the contacts 264 on the disposable portion 252. The contacts 270 on the reusable portion are in turn wired to the main circuit board 276. Therefore, once the disposable portion 252 is docked in the reusable portion of the calorimeter, the thin ultrasonic transducer 260 is in electrical communication with the main circuit board 276. However, because the thin transducer 260 and its associated wiring are mounted in the disposable portion 252, the entire transducer may be disposed along with a remainder of the disposable portion. This prevents any concerns about contact of the user's breath with the transducer. Alternatively, the disposable portion may be designed so as to be cleaned according to a specified cleaning procedure that does not harm the transducers.

A lower thin ultrasonic transducer 278 is disposed on the upper surface of the floor 258 of the disposable portion 252, aligned with a flow tube 262, and cooperates with the upper transducer 260 to measure flow through the flow tube. Like the upper transducer 260, the lower transducer 278 is wired to electrical contacts 280 that abut electrical contacts 282 disposed on the rear wall 272 of the recess. A passage 284 is defined in the floor 258 of the disposable portion 252 so as to allow inhalation and exhalation to flow in and out of the disposable portion. This passage communicates with a large flow area 286 in the bottom of the reusable portion 274 of the calorimeter. As an alternative, the entire lower portion of the reusable portion may be removed so that the passage in the floor of the disposable portion has no part of the reusable portion directly below it. In this way, inhalation and exhalation flowing through the passageway flows directly to and from the surrounding ambient air without coming into contact with any part of the reusable portion.

This embodiment of the calorimeter also uses an alternative version of an oxygen sensor 288. In this version, the LED and photodiode portions of the oxygen sensor are incorporated in a sensor package 290 disposed in the rear wall 272 of the recess approximately midway between the upper and lower ends of the recess. The remainder of the oxygen sensor 288 forms a part of the disposable portion 252 and is referred to as the fluorescence portion 292. The fluorescence portion 292 consists of a light pipe 294 extending from the rear surface 296 of the outer shell 256 adjacent the sensor package 290 into the wall 298 of the flow tube 262. The fluorescence material 300 is disposed on the end of the light pipe 294 so that it is in contact with the gases flowing through the flow tube 262. The light pipe 294 conducts light traveling to and from the fluorescence material 300. This configuration allows disposal of the portion of the oxygen sensor 288 that comes into contact with the user's breath. As shown, the fluorescence material 300 is positioned approximately midway in the flow tube 262. This provides a benefit in that the portion of the flow that is being sensed by the oxygen sensor is approximately at the midpoint of the portion of the flow that is being measured for flow speed. This allows better time correlation of the flow and oxygen concentration measurements.

Referring now to FIG. 9, yet another alternative version of an oxygen sensor 302 is disclosed. In this version, the sensor package 304 is interconnected with a circuit board 306. The sensor package 304 includes the light emitting diode, LED, and photodiode of the earlier discussed embodiment. Pieces of fluorescence material 308 are disposed in the wall 310 of a flow tube 312, a portion of which is shown. Light travels between the sensor package 304 and the fluorescence material 308 across a small air gap. Obviously, this configuration requires a different construction of the flow tube. However, it allows simple and compact construction of an oxygen sensor with a disposable portion.

An important factor in the disclosed oxygen sensors with disposable portions is calibration. A fluorescence quench oxygen sensor of the type described herein typically requires careful calibration for the chemistry used. However, highly accurate and repeatable application of fluorescence material reduces the need for individualized calibration. Instead, the sensor package may include a mathematical model of the fluorescence material such that accurate oxygen concentration measurements may be made with disposable fluorescence materials. As discussed previously, calibration of the oxygen sensor during inhalations further improves accuracy.

Figure 21:
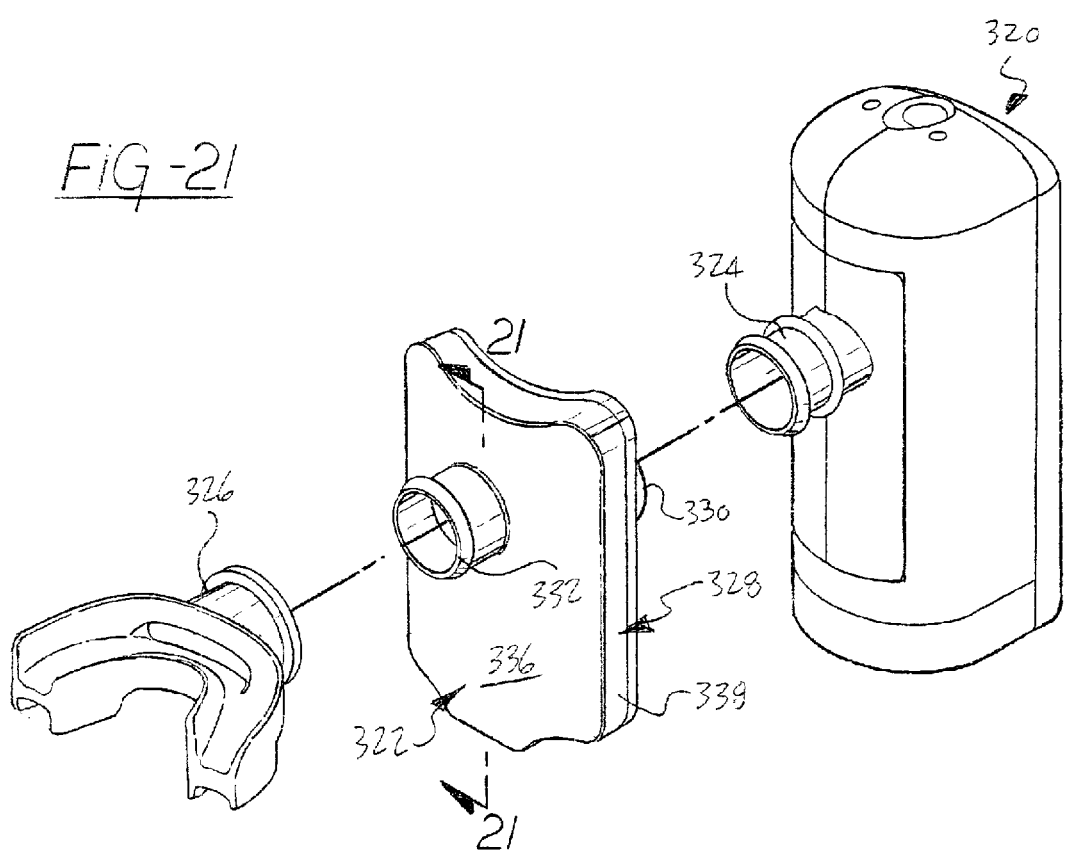
FIG. 21 is a perspective view in partially exploded form of a respiratory calorimeter according to the present invention and a hygiene filter module for use with the calorimeter.

Referring now to FIG. 21, an alternative approach to improved sanitation for use with a calorimeter according to the present invention is illustrated. A calorimeter body according to any of the embodiments of the present invention is generally shown at 320. A germicidal filtration module 322 connects between the inlet conduit 324 of the calorimeter 320 and the respiratory connector, here shown as a mouthpiece 326. Referring to both FIGS. 21 and 22, the module 322 has a filter housing 328 with a calorimeter port 330 defined on one side and a respiration port 332 defined in the other. The calorimeter port 330 mates with the inlet conduit 324 of the calorimeter while the respiration port 332 mates with the respiration connector. The housing 328 may be of various shapes, including the generally rectangular configuration shown in FIG. 21. A piece of biological filter material 334, such as Filtrete® from 3M, extends within the housing 328 such that air flowing between the respiration port 332 and the calorimeter port 330 must pass through the filter material. The filter material is operable to remove pathogens thereby preventing pathogens from flowing from the respiration connector into the calorimeter. In this way, the calorimeter remains sanitary during use. Each subsequent user uses a new filter module 322 with the used module either being retained by that user or disposed.

Figure 22:
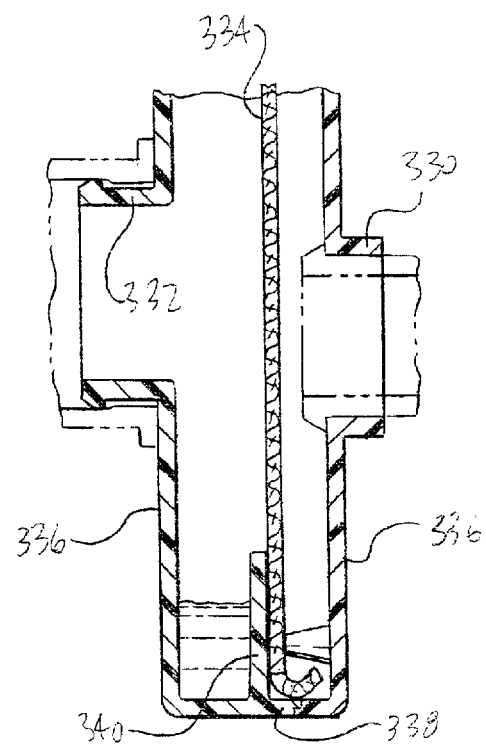
FIG. 22 is a cross sectional view of the hygiene filter module of FIG. 21.

Referring again to FIG. 22, it can be seen that the module 322 has two generally parallel and spaced apart side walls 336 with a perimeter edge 338 interconnecting the side walls 336. The filter material is generally parallel to the side walls 336 and extends between the perimeter edges 338. As best shown in FIG. 22, a saliva retention wall 340 extends upwardly from the bottom edge adjacent the filter material 334 on the side of the filter material closest to the respiration connector 326. During use of the calorimeter, especially with a mouthpiece, saliva is entrained in the exhalation breath and is preferably not introduced into the calorimeter. Much of the entrained saliva will flow along the lower edge of the respiration port 332 and down the inside of the side wall 336 where it will collect in the area between the saliva retaining wall 340 and the side wall 336, as shown. Also, some entrained saliva may contact the filter material and then fall downwardly to collect in the saliva trap. This arrangement avoids the need for the saliva trap discussed earlier in the disposable portion of the calorimeter, though it may be retained for other purposes.

Figure 23:
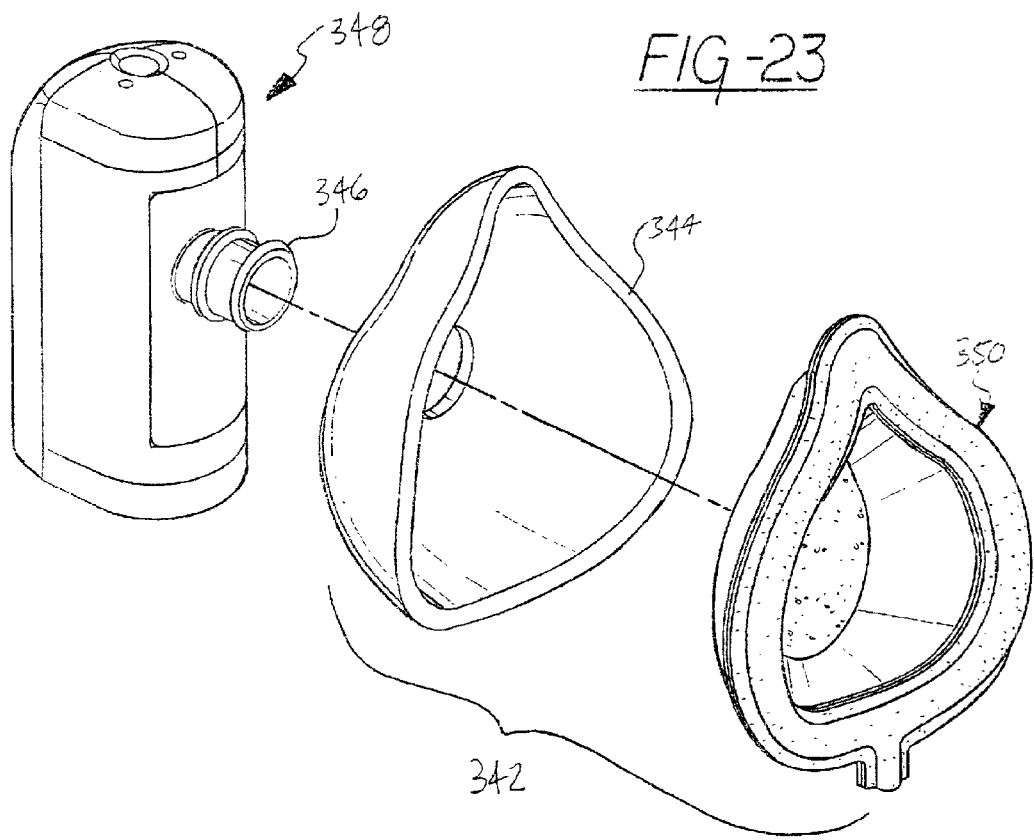
FIG. 23 is a perspective view in partially exploded form of a respiratory calorimeter according to the present invention with an alternative embodiment of a mask incorporating a hygiene barrier.
Figure 24:
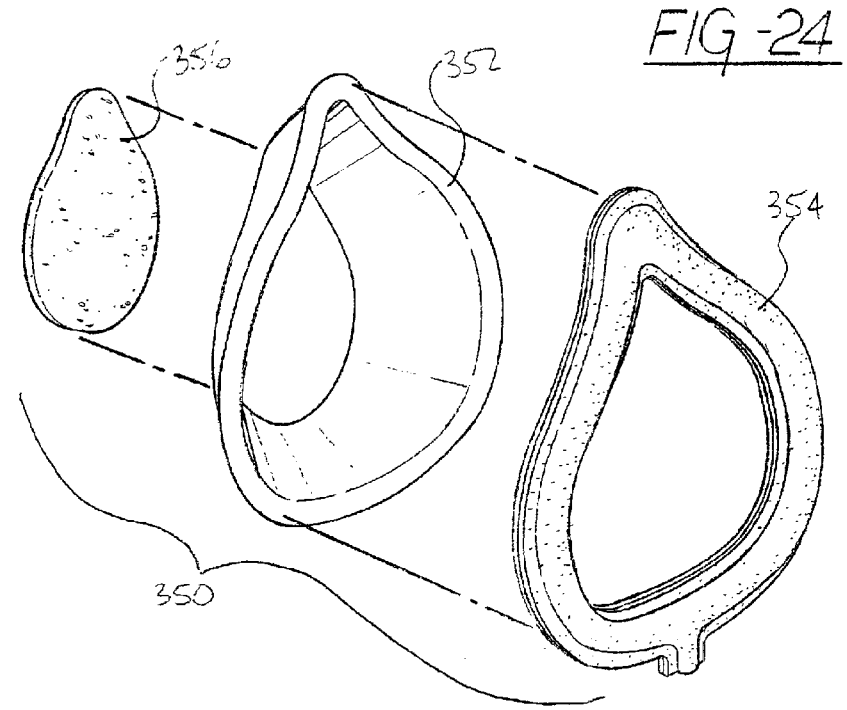
FIG. 24 is a perspective view in exploded form of the disposable portion of the mask of FIG. 23.

Referring now to FIGS. 23 and 24, an alternative hygiene barrier arrangement is illustrated. In the configurations of FIGS. 23 and 24, a mask 342 is provided instead of a mouthpiece. In this case, the mask 342 consists of a semi-rigid outer shell 344 that interconnects with the inlet conduit 346 of the calorimeter 348. The mask shell 344 may be made of any of a variety of materials, including polystyrene. The mask shell 344 is preferably ultrasonically bonded to the inlet conduit 346 of the disposable portion of the calorimeter to provide an air-tight seal. A disposable mask liner 350 is inserted into the mask shell 344. The mask liner 350 includes a liner shell 352 which overlies a portion of the masked shell 344, a face seal 354 to seal the mask 342 to the face of the user, and a hygiene barrier 356 that filters all gases flowing into and out of the calorimeter. Once again, the hygiene barrier 356 may be a material such as Filtrete® by 3M. The face seal 354 preferably is an inflated sealed film that easily forms to the shape of the user's face providing a secure seal. The face seal 354 is securely attached, such as by a cement bond, to the liner shell 352, which is preferably a vacuum formed plastic. The hygiene barrier 356 is securely interconnected with the liner shell 352 such as by an ultrasonic bond.

Figure 25:
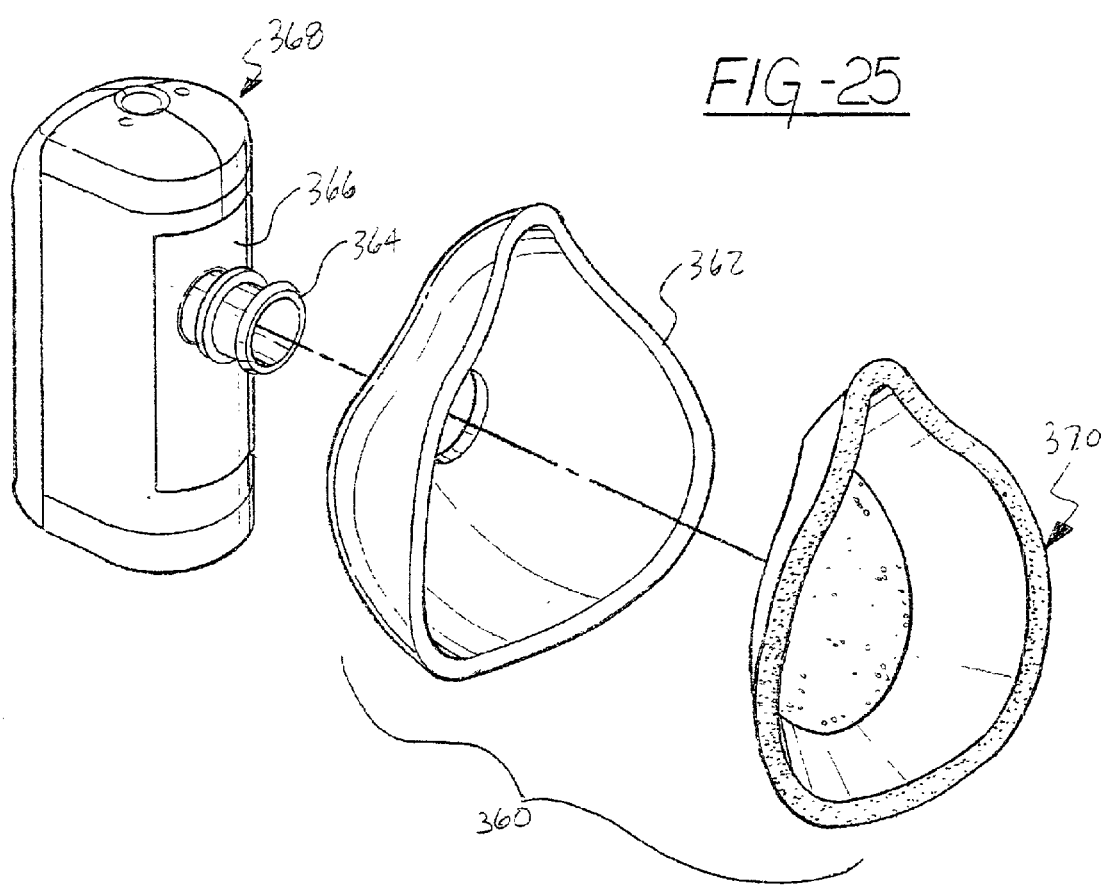
FIG. 25 is a perspective view in partially exploded form of a respiratory calorimeter according to the present invention with a second alternative embodiment of a mask incorporating a hygiene barrier.
Figure 26:
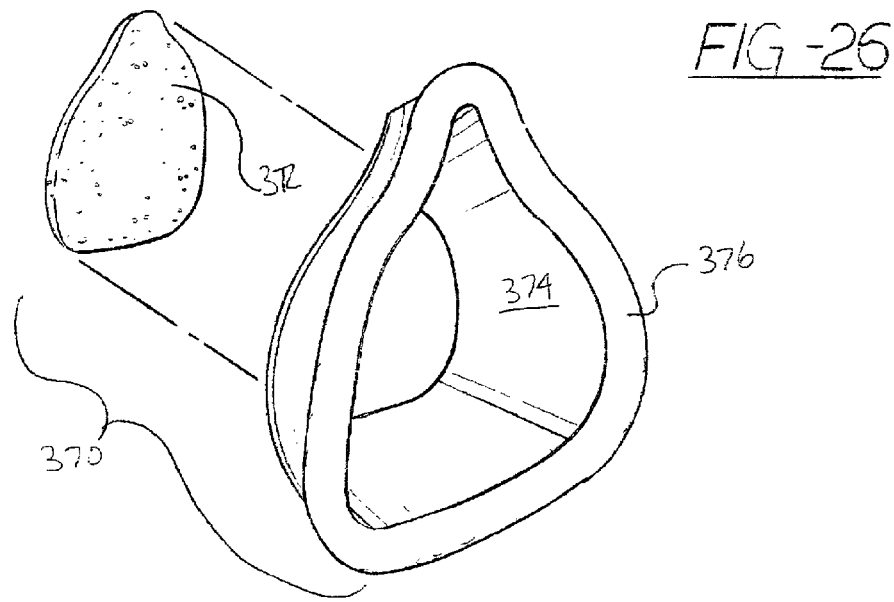
FIG. 26 is a perspective view in exploded form of the disposable portion of the mask of FIG. 25.

Referring now to FIGS. 25 and 26, an alternative filtered mask design 360 is disclosed. Similar to the previous version, a semi-rigid mask shell 362 is interconnected with the inlet conduit 364 of the disposable portion 366 of the calorimeter 368. A mask liner 370 inserts into the shell and is disposable. The mask liner 370 includes a piece of hygiene barrier material 372 such as Filtrete® which is interconnected, such as by insert molding, to a liner shell 374 which is in turn molded with an injection molded-type face seal 376 of elastomer material. The face seal 376 securely seals to the face of the user thereby preventing leakage.

Because users vary in the size and shape of their face, mask shells and/or mask liners may be provided in a variety of sizes and shapes to suit various users. Also, as will be clear to those of skill in the art, other designs of masks and filter housings may also be used wherein the breath is filtered. According to the present invention, it is preferred that a relatively large piece of hygiene barrier material is used so as to prevent a pressure drop across the material. In this way, the barrier material does not significantly increase the resistance of flow through the calorimeter and thereby does not cause the expenditure of additional energy during use of the calorimeter.

As an alternative, a mask according to the present invention may include a nares spreader for opening the nostrils of a user, thereby reducing the effort associated with breathing through the mask. As one approach, adhesive pads may be provided inside the nose portion of the mask. The pads are pressed into contact with the nose of the user and, when released, the mask opens the nasal passages.

Other Alternative Designs

The above discussed embodiments of the present invention may be altered in various ways without departing from the scope or teaching of the present invention. The following are a number of alternative designs and alterations on the preferred embodiments.

While the preferred embodiments of the present invention utilize a fluorescence based oxygen sensor, other approaches may also be used. Other possible oxygen sensor methods include solid oxide sensors if adapted for rapid response, e.g. using zirconium oxide; or other electrochemical sensors. Molecular fluorescence, e.g. laser-induced fluorescence, may also be used. For example, laser radiation can be sent along the flow path, and fluorescence detected using a sensor on the side of the flow path, or light guides used to convey fluorescence to a detector in the reusable body of the device. Similarly Raman spectroscopy, including nonlinear Raman spectroscopy, may be used. A laser beam might pass along the flow path, with detection in a direction at some angle to the beam. Narrow-band filters, to remove laser radiation, would aid in detection, as would phase-sensitive detection. Other oxygen-detection techniques include laser absorption; chromatography methods; sensors based on diffusion rates through films; or fast-response colorimetric sensors, e.g. using the photoabsorption or photoreflectance changes of films, such as transition metal complexes, in the presence of oxygen. IR emission from vibrationally excited molecules may be detected. Laser radiation might be used for selective vibrational or vibronic excitation of molecules. Also, phosphorescent compounds, e.g. platinum and gold complexes, are useful for oxygen detection, as described in e.g. A. Mills, Platinum Metals Review, June 1997; U.S. Pat. No. 5,119,463; and elsewhere. Selective (e.g. laser) photoionization of molecules, followed by detection of photoions and electrons, may provide a photocurrent proportional to molecular concentration. The ultrasonic spectrum of the respired gas may also contain molecular information, related to concentration, particularly if wide-spectrum response (up to 10 MHz and higher frequencies) micromachined ultrasonic transducers are used.

As mentioned previously, the preferred oxygen sensing capability of the present invention may be supplemented by the addition of a carbon dioxide sensor. Other gases may be sensed as well. Generically, oxygen sensors, carbon dioxide sensors, as well as other gas sensors are referred to herein as component gas concentration sensors. Carbon dioxide sensing may be accomplished in a variety of ways. Carbon dioxide concentration may be measured using a carbon dioxide scrubber in combination with volume measurements as described in some of Mault's earlier patents and applications. Also as described in some of Mault's earlier patents and applications, metabolic calculations may be made based on measurement of carbon dioxide, without the measurement of oxygen. A calorimeter according to the present invention may be constructed with any of a variety of carbon dioxide sensors, such as a capnometer, and without an oxygen sensor. Carbon dioxide may be measured using IR absorption, using the strong carbonyl absorption, or other analytical techniques, such as those listed earlier for oxygen. Carbon dioxide and oxygen sensors may be combined into the same package for a combined fluorescent quenching sensor, for example, using selectively permeable membranes or different fluorescent compounds.

As other approaches to indirect calorimetry, the approaches disclosed in Mault's PCT WO 00/07498, incorporated herein by reference, may be incorporated into a calorimeter constructed according to the present invention. Specifically, the oxygen sensor could be omitted and the mass flow determined based on either approach in WO 00/07498. This avoids the cost associated with the oxygen sensor. Alternatively, the mass flow based approach may be used as a supplement to one or more gas concentration sensors.

As yet another approach to indirect calorimetry, a carbon dioxide scrubber may be used to remove substantially all of the carbon dioxide from the inhalation and/or exhalation flow, and the difference in flow volume measured to determine the amount of carbon dioxide produced. From this, metabolic rate may be determined. This avoids the need for component gas concentration sensors. Instead, only a scrubber and a two way flow meter are required. This approach is further disclosed in Mault's U.S. Pat. No. 5,179,958. The above described embodiments of the present invention may easily be configured to utilize this approach. For example, a scrubber module may be inserted in the flow path between the disposable portion and the respiratory connector, as part of or in place of the hygiene filter module of FIG. 21. Alternatively, the disposable portion may be designed to include scrubber material in an extended flow path.

Other flow sensing methods are possible, for example, using the cooling rate or heat dissipation of objects in the flow path. Hot wire mass sensors are known in the art, along with analogous devices using semiconductors (e.g. silicon), ceramics, etc., e.g. hot film semiconductor sensors. Other methods include turbines or impellers; noise levels as gas flows e.g. around an obstruction or through an aperture; distortion of e.g. an aperture or membrane due to the pressure difference between each side, which could be monitored with high precision using e.g. laser reflection; or distortion of other structures placed in the flow path, e.g. micromachined rods; and thermoelectric gas flow sensors. Direct pressure difference measurements may be used e.g. using micromachined pressure sensors at either end of a flow path. Other configurations of ultrasonic transducers are also possible. For example, three transducers could be mounted at the edges of a gas flow path, forming a V-shaped configuration. The transducer at the center of the V would transmit to two other transducers mounted on the opposite side of the flow path, spaced an equal direction on either side of the center transducer. The difference between the two transmission times is related to gas flow velocity. Other flow measurement techniques include thermal imaging of the flow path, followed by image analysis; the Doppler shift of transmitted ultrasonic signals; or Doppler shift or broadening of molecular or atomic absorption or emission bands, as measured using e.g. laser radiation.

The problems related to moisture may be reduced by protecting the oxygen sensor from moisture, or removing the moisture from the air flow. For example, moisture removal may include passing the exhaled gas through or past, foam sheets (possibly fabricated to include a drying mechanism); zeolites; molecular sieves; membranes; chemical drying agents, e.g. silica gel. These moisture-removing means could be mounted within a removable part, for easy replacement. The oxygen sensor may be protected from the effects of moisture using e.g. a water-impermeable, oxygen permeable membrane placed over the oxygen sensor, or hydrophobic films placed over the sensor Other methods for measuring the temperature of the gas flow include detecting thermal distortion of micromachined structures in the flow path, e.g. of multilayer membranes using optical or electrical methods; or by monitoring temperature-dependent molecular or atomic properties, e.g. emission or absorption wavelengths. Computer modeling of respired air temperature as it passes through the device may be combined with spot temperature measurements to obtain a detailed temperature distribution. Thermoelectric sensors, thermistors, pyroelectric sensors, thermopiles, etc. may be used. The temperature dependence of the ultrasonic spectrum of inhaled air may be monitored. Thermal imaging of the flow path may also be useful.

In addition to the present embodiment, there are many other adaptations of the present invention (sometimes referred to as "the device" below) which may be useful. For example, the air vents of the device may be replaced with a connector adapted to send exhaled air to other analytical devices for further analysis. Other gas sensors may be included in the flow path. Respiration components of interest include: oxygen and carbon dioxide (as previously discussed), nitric oxide, other radicals, ketones (e.g. acetone), aldehydes (e.g. acetaldehyde), alkanes (e.g. pentane), other hydrocarbons, esters, hydrogen sulfide, indicators of lung disease or cancer, other volatile organic compounds, gases produced by bacteria (e.g. sulfides). Detectors for radioisotopes of inert gases (e.g. xenon) may be included for quantitative lung function tests.

The embodiments of the present invention thus far described assume inhalation of atmospheric gases. However, the present invention is equally applicable to inhalation of other gas mixtures from a source of respiratory gases. For example, a connector may be provided on the bottom the calorimeter, in addition to or in place of the vents, so that the calorimeter may be interconnected to a source and/or sink or respiratory gases other than atmospheric. One application of such an approach is the use of a calorimeter according to the present invention in an anesthesiology or assisted breathing apparatus. The flow through the calorimeter may be assisted in either direction and pressures other than atmospheric may be utilized. Obviously, sensors would be used to monitor these non-atmospheric conditions so that the proper calculations of metabolic rate and other respiratory factors may be made. Additional aspects concerning the use of a calorimeter according to the present invention as part of a mechanical ventilation system will be clear from a review of Mault's provisional patent application Nos. 60/179,906 filed Feb. 2, 2000 and 60/179,961 filed Feb. 3, 2000, both of which are incorporated herein by reference.

Breath profile analysis may be used e.g. in order to determine end tidal volumes precisely, or investigate breathing anomalies due to e.g. blockages. The device may communicate with other physiological sensors, and/or be in communication with other electronic devices, e.g. for data transmission, data analysis, display, feedback, or other uses. Data from spirometry/indirect calorimetry obtained using the present invention may be combined with other physiological or environmental data for analysis. The device may produce electromagnetic radiation for powering physiological sensors embedded in the body of the person under test, e.g. micromachined ultrasonic flow sensors placed near the lungs, arteries, or veins. Also, a calorimeter according to the present invention may include other sensors or physiological monitors. For example, a positioning system, based on GPS, telemetry, cellular phone signals, or others may be incorporated to provide information on the location of a user. The calorimeter could then be used during an exercise session that requires moving around, and the positioning system would provide information on position while the calorimeter provides metabolic information, allowing correlations and analysis.

While the present invention is preferably directed to the measuring respiratory parameters such as metabolic rate, a simpler flow meter version of the present invention is also of merit. The present invention, with the oxygen sensor removed, and possibly simplified in other ways, provides an excellent flow meter for such applications as measuring flow rate and volume in lung capacity tests. The flow meter could also be used in other applications.

A calorimeter according to the present invention may be incorporated into a weight or health management system, which may include a personal digital assistant (PDA) for data entry, communication, physiological monitoring, feedback, and data processing. This and other uses for the present invention are disclosed in Mault's provisional applications Ser. Nos. 60/165,988 filed Nov. 17, 1999; 60/167, 276 filed Nov. 24, 1999; 60/177,016 filed Jan. 19, 2000.

Other physical configurations of the present invention are possible without departing from the scope or teaching. For example, the display for displaying metabolic parameters may be repositioned, reconfigured, or supplemented. The display could be moved to a position such that the subject could see the display during a test. Alternatively, a separate display, which received data either through a wire or wirelessly from the calorimeter, may be provided so that a user may position the display where it is easy to read during a test. The display could also or alternatively be viewed by another person such as a health professional. Viewing the display during testing could allow the user to witness metabolic changes due to changes in their activity level, relaxation level, or for other reasons. For example, the calorimeter and the display, or other feedback device, could be used a biofeedback system for helping people to reach certain levels of relaxation. Breathing therapy and training could also be administered using the calorimeter to monitor breathing rate, volume, and other factors.

As yet another alternative, an artificial "nose" may be provided for use with or as part of the calorimeter. An artificial "nose" conditions the inhalations and/or exhalations so as to control humidity or temperature. This may be advantageous for some applications.

What is claimed is:

1. An indirect calorimeter, comprising:
   a respiratory connector configured to be supported in contact with a subject so as to pass inhaled and exhaled gases as said subject breathes;
   a hygiene barrier module operatively connected to said respiratory connector, such that said inhaled and exhaled gases pass therethrough said hygiene barrier module for blocking a predetermined pathogen from said exhaled gases;

a flow pathway operatively connected to said hygiene barrier module for receiving and passing said inhaled and exhaled gases, said flow pathway having a first end in fluid communication with said respiratory connector and a second end in fluid communication with a source and sink for respiratory gases, said flow pathway comprising: (1) a flow tube through which said inhaled and exhaled gases pass, (2) an outer housing surrounding said flow tube, and (3) a chamber disposed between said flow tube and said first end, said chamber being a concentric chamber surrounding one end of said flow tube and being defined between said flow tube and said outer housing;

a flow meter configured to generate electrical signals as a function of an instantaneous flow volume of said inhaled and exhaled gases passing through said flow pathway;

a component gas concentration sensor operable to generate electrical signals as a function of an instantaneous fraction of a predetermined component gas in said exhaled gases passing through said flow pathway; and a computation unit operable to receive said electrical signals from said flow meter and said concentration sensor and to calculate at least one respiratory parameter for said subject as said subject breathes through said calorimeter.

2. The calorimeter according to claim 1, wherein said hygiene barrier module includes a hygiene barrier housing including two generally parallel and spaced apart side walls and a hygiene barrier disposed between said side walls.

3. The calorimeter according to claim 2, wherein said hygiene barrier is a filtering material.

4. The calorimeter according to claim 2, wherein said hygiene barrier housing includes a lower wall and a saliva retention wall extending upwardly from said lower wall and adjacent said hygiene barrier to form a saliva trap.

5. The calorimeter according to claim 2, wherein said hygiene barrier module includes a respiration port for operatively connecting said hygiene barrier module to a corresponding port for said respiratory connector and a calorimeter port for operatively connecting said hygiene barrier module to a corresponding inlet conduit in fluid communication with said flow pathway.

6. The calorimeter according to claim 1, wherein said respiratory connector is a mask.

7. The calorimeter according to claim 1, wherein said hygiene barrier module and said respiratory connector are disposable.

8. The calorimeter according to claim 1, wherein said respiratory connector is a mouthpiece.

9. An indirect calorimeter, comprising:

a respiratory connector configured to be supported in contact with a subject so as to pass inhaled and exhaled gases as said subject breathes;

a flow pathway operatively connected to said respiratory connector for receiving and passing said inhaled and exhaled gases, said flow pathway having a first end in fluid communication with said respiratory connector and a second end in fluid communication with a source and sink for respiratory gases, said flow pathway comprising: (1) a flow tube through which said inhaled and exhaled gases pass, (2) an outer housing surrounding said flow tube, and (3) a chamber disposed between said flow tube and said first end, said chamber being a concentric chamber surrounding one end of said flow tube and being defined between said flow tube and said outer housing;

a hygiene barrier positioned such that said inhaled and exhaled gases pass therethrough said hygiene barrier for blocking a predetermined pathogen from said exhaled gases;

a flow meter configured to generate electrical signals as a function of an instantaneous flow volume of said inhaled and exhaled gases passing through said flow pathway;

a component gas concentration sensor operable to generate electrical signals as a function of an instantaneous fraction of a predetermined component gas in said exhaled gases passing through said flow pathway; and a computation unit operable to receive said electrical signals from said flow meter and said concentration sensor and to calculate at least one respiratory parameter for said subject as said subject breathes through said calorimeter.

10. The calorimeter according to claim 9, wherein said respiratory connector is a mask, and said hygiene barrier is disposed within said mask.

11. The calorimeter according to claim 9, wherein said hygiene barrier is housed within a hygiene barrier module operatively connected between said respiratory connector and said flow pathway, said hygiene barrier module including a hygiene barrier housing including two generally parallel and spaced apart side walls with said hygiene barrier disposed between said side walls.

12. The calorimeter according to claim 11, wherein said hygiene barrier is a filtering material.

13. The calorimeter according to claim 11, wherein said hygiene barrier housing includes a lower wall and a saliva retention wall extending upwardly from said lower wall and adjacent said hygiene barrier to form a saliva trap.

14. The calorimeter according to claim 11, wherein said hygiene barrier module includes a respiration port for operatively connecting said hygiene barrier module to a corresponding port for said respiratory connector and a calorimeter port for operatively connecting said hygiene barrier module to a corresponding inlet conduit in fluid communication with said flow pathway.

15. The calorimeter according to claim 14, wherein said respiratory connector is a mouthpiece.

16. The calorimeter according to claim 14, wherein said respiratory connector and said hygiene barrier module are disposable.

17. The calorimeter according to claim 14, wherein said respiratory connector is a mask.

18. The calorimeter according to claim 10, wherein said mask further includes a mask shell and a mask liner inserted in said mask shell.

19. The calorimeter according to claim 18, wherein said hygiene barrier is a filtering material.

20. The calorimeter according to claim 19, wherein said mask shell and an inlet conduit for said flow pathway are integral and formed as one piece.

21. The calorimeter according to claim 20, wherein said mask shell, said inlet conduit and said flow pathway are disposable.

22. An indirect calorimeter, comprising:

a respiratory connector configured to be supported in contact with a subject so as to pass inhaled and exhaled gases as said subject breathes;

a hygiene barrier disposed within said respiratory connector, such that substantially all of said inhaled and exhaled gases pass through said hygiene barrier, and said hygiene barrier operatively passes said inhaled and exhaled gases therethrough while blocking a predetermined pathogen in said exhaled gases;

a flow pathway operable to receive and pass said inhaled and exhaled gases, said flow pathway having a first end in fluid communication with said respiratory connector and a second end in fluid communication with a source and sink for respiratory gases, said flow pathway comprising: (1) a flow tube through which said inhaled and exhaled gases pass, (2) an outer housing surrounding said flow tube, and (3) a chamber disposed between said flow tube and said first end, said chamber being a concentric chamber surrounding one end of said flow tube and being defined between said flow tube and said outer housing;

a flow meter configured to generate electrical signals as a function of an instantaneous flow volume of said inhaled and exhaled gases passing through said flow pathway;

a component gas concentration sensor operable to generate electrical signals as a function of an instantaneous fraction of a predetermined component gas in said exhaled gases passing through said flow pathway; and a computation unit operable to receive said electrical signals from said flow meter and said concentration sensor and to calculate at least one respiratory parameter for said subject as said subject breathes through said calorimeter.

23. The calorimeter according to claim 22, wherein said respiratory connector includes:

a mouthpiece; and a hygiene barrier module including an inlet port for operatively connecting said hygiene barrier module to said mouthpiece and a connecting port for operatively connecting said respiratory connector to a corresponding inlet conduit in fluid communication with said flow pathway, said hygiene barrier being housed within said hygiene barrier module.

24. The calorimeter according to claim 22, wherein said respiratory connector is a mask.

25. The calorimeter according to claim 24, wherein said hygiene barrier is a filtering material.

26. The calorimeter according to claim 25, wherein said respiratory connector is disposable.

27. The calorimeter according to claim 24, wherein said mask further includes a mask shell and a mask liner inserted in said mask shell.

28. The calorimeter according to claim 27, wherein said mask shell is integral and formed as one with an inlet conduit in fluid communication with said flow pathway.

29. The calorimeter according to claim 28, wherein said hygiene barrier is a filtering material.

30. The calorimeter according to claim 29, wherein said mask liner is disposable, and said integral mask shell and inlet conduit are disposable.

31. The calorimeter according to claim 23, wherein said hygiene barrier is a filtering material.

32. The calorimeter according to claim 23, wherein said hygiene barrier module includes a hygiene barrier module includes a hygiene barrier housing including two generally parallel and spaced apart side walls with said hygiene barrier disposed between said side walls.

33. The calorimeter according to claim 32, wherein said hygiene barrier housing includes a lower wall and a saliva retention wall extending upwardly from said lower wall and adjacent said hygiene barrier to form a saliva trap.

34. An indirect calorimeter, comprising:

a flow tube configured to pass respiratory gases of a subject;

a flow meter coupled to said flow tube, said flow meter being configured to generate a first signal associated with said respiratory gases passing through said flow tube;

a component gas concentration sensor coupled to said flow tube, said component gas concentration sensor being configured to generate a second signal associated with said respiratory gases passing through said flow tube; and a computation unit coupled to said flow meter and said component gas concentration sensor, said computation unit being configured to process said first signal and said second signal to determine a volume of said respiratory gases passing through said flow tube and a concentration of oxygen in said respiratory gases passing through said flow tube, said computation unit being configured to determine an amount of oxygen consumed by said subject based on said volume of said respiratory gases passing through said flow tube and said concentration of oxygen in said respiratory gases passing through said flow tube, said computation unit being configured to determine an amount of carbon dioxide produced by said subject based on said volume of said respiratory gases passing through said flow tube and said concentration of oxygen in said respiratory gases passing through said flow tube, said computation unit being configured to determine a resting metabolic rate for said subject based on said amount of oxygen consumed and said amount of carbon dioxide produced.

35. The calorimeter according to claim 34, wherein said flow meter is an ultrasonic flow meter.

36. The calorimeter according to claim 34, wherein said component gas concentration sensor is an oxygen sensor.

37. The calorimeter according to claim 34, wherein said computation unit is further configured to determine said resting metabolic rate for said subject based on said amount of oxygen consumed and an assumed respiratory quotient for said subject.

38. The calorimeter according to claim 37, wherein said assumed respiratory quotient ranges from 0.7 to 1.1.

39. The calorimeter according to claim 38, wherein said assumed respiratory quotient is 0.85.

40. An indirect calorimeter, comprising:

a first sensor configured to generate an output associated with a volume of inhaled gases of a subject and a volume of exhaled gases of said subject;

a second sensor configured to generate an output associated with a fraction of oxygen in said exhaled gases, said second sensor being a fluorescence quench oxygen sensor; and a processing unit coupled to said first sensor and said second sensor, said processing unit being configured to process said output of said first sensor and said output of said second sensor to determine an amount of carbon dioxide produced by said subject.

41. The calorimeter according to claim 40, wherein said first sensor is a flow meter.

42. The calorimeter according to claim 41, wherein said flow meter includes a plurality of ultrasonic transducers.

43. The calorimeter according to claim 40, wherein said processing unit is configured to process said output of said first sensor and said output of said second sensor to determine an amount of oxygen consumed by said subject.

44. The calorimeter according to claim 43, wherein said processing unit is configured to determine a resting metabolic rate for said subject based on said amount of oxygen consumed and said amount of carbon dioxide produced.

45. The calorimeter according to claim 40, further comprising:
a flow tube configured to pass said inhaled gases and said exhaled gases as said subject breathes, said first sensor and said second sensor being coupled to said flow tube.

46. The calorimeter according to claim 45, further comprising:
a hygiene barrier module coupled to said flow tube, said hygiene barrier module being configured to block a predetermined pathogen from said exhaled gases.

47. An indirect calorimeter, comprising:
means for generating a first output associated with a volume of respiratory gases of a subject;
means for generating a second output associated with a concentration of oxygen in said respiratory gases; and
means for processing said first output and said second output to determine a resting metabolic rate for said subject, said means for processing said first output and said second output including:
means for determining an amount of oxygen consumed by said subject based on said volume of said respiratory gases and said concentration of oxygen in said respiratory gases; and
means for determining said resting metabolic rate based on said amount of oxygen consumed and an assumed respiratory quotient for said subject.

48. The calorimeter according to claim 47, wherein said means for processing said first output and said second output further includes:
means for determining an amount of carbon dioxide produced by said subject based on said volume of said respiratory gases and said concentration of oxygen in said respiratory gases; and
means for determining said resting metabolic rate based on said amount of oxygen consumed and said amount of carbon dioxide produced.

49. The calorimeter according to claim 47, wherein said assumed respiratory quotient ranges from 0.7 to 1.1.

50. The calorimeter according to claim 49, wherein said assumed respiratory quotient is 0.85.

51. An indirect calorimeter, comprising:
a flow tube configured to pass inhaled gases and exhaled gases of a subject;
a flow meter coupled to said flow tube, said flow meter being configured to generate an output associated with a volume of said inhaled gases and a volume of said exhaled gases;
a component gas concentration sensor coupled to said flow tube, said component gas concentration sensor being configured to generate an output associated with a concentration of oxygen in said exhaled gases;
a temperature sensor configured to generate an output associated with ambient temperature:
a pressure sensor configured to generate an output associated with ambient pressure;
a humidity sensor configured to generate an output associated with relative humidity; and
a computation unit coupled to said flow meter, said component gas concentration sensor, said temperature sensor, said pressure sensor, and said humidity sensor said computation unit being configured to process said output of said flow meter and said output of said component gas concentration sensor to determine at least one respiratory parameter for said subject, said computation unit being configured to process said output of said temperature sensor, said output of said pressure sensor, and said output of said humidity sensor to determine said at least one respiratory parameter.

52. The calorimeter according to claim 51, wherein said component gas concentration sensor is an oxygen sensor.

53. The calorimeter according to claim 52, wherein said oxygen sensor is a fluorescence quench oxygen sensor.

54. The calorimeter according to claim 51, wherein said output of said component gas concentration sensor is further associated with a concentration of oxygen in said inhaled gases.

55. The calorimeter according to claim 51, wherein said computation unit is configured to process said output of said flow meter and said output of said component gas concentration sensor to determine an amount of oxygen consumed by said subject and an amount of carbon dioxide produced by said subject, said computation unit being configured to determine said at least one respiratory parameter based on said amount of oxygen consumed and said amount of carbon dioxide produced.

56. The calorimeter according to claim 55, wherein said computation unit is configured to determine said amount of oxygen consumed based on said volume of said inhaled gases, said volume of said exhaled gases, and said concentration of oxygen in said exhaled gases.

57. The calorimeter according to claim 55, wherein said computation unit is configured to determine said amount of carbon dioxide produced based on said volume of said inhaled gases, said volume of said exhaled gases, and said concentration of oxygen in said exhaled gases.

58. The calorimeter according to claim 51, further comprising;
a respiratory connector coupled to said flow tube, said respiratory connector being configured to be supported in contact with said subject so as to pass said inhaled gases and said exhaled gases.

59. The calorimeter according to claim 51, wherein said flow meter is an ultrasonic flow meter.

60. The calorimeter according to claim 58, further comprising:
a hygiene barrier module coupled to said respiratory connector and said flow tube, said hygiene barrier module being configured to block a predetermined pathogen from said exhaled gases.

61. The calorimeter according to claim 22, wherein said respiratory connector includes:
a respiratory connector housing including an inlet port and a connecting part in fluid communication with said flow pathway; and
a mouthpiece integral with said inlet port,
said hygiene barrier being disposed between said mouthpiece and said connecting port for operatively passing said inhaled and exhaled gases therethrough while blocking said predetermined pathogen in said exhaled gases.

62. The calorimeter according to claim 61, wherein said hygiene barrier is a filtering material.

* * * * *